US006900017B2

(12) United States Patent
Sharma et al.

(10) Patent No.: US 6,900,017 B2
(45) Date of Patent: May 31, 2005

(54) HUMAN HEMATOPOIETIC GROWTH REGULATORY GENE AND USES

(75) Inventors: Arun Sharma, Oak Park, IL (US); Ronald Hoffman, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 151 days.

(21) Appl. No.: 10/043,774

(22) Filed: Jan. 10, 2002

(65) Prior Publication Data

US 2003/0129599 A1 Jul. 10, 2003

(51) Int. Cl.⁷ .......................... C12Q 1/68; C12N 1/00; C12N 5/10; C12N 15/12; C12N 15/63

(52) U.S. Cl. ..................... 435/6; 435/243; 435/320.1; 435/325; 435/419; 536/23.5

(58) Field of Search ....................... 536/23.5, 24.31; 435/320.1, 325, 419, 243, 6, 29

(56) References Cited

U.S. PATENT DOCUMENTS

| 4,683,195 A | 7/1987 | Mullis et al. |
| 4,683,202 A | 7/1987 | Mullis et al. |

FOREIGN PATENT DOCUMENTS

| WO | WO0032039 | * 6/2000 |

OTHER PUBLICATIONS

Sharma et al, Blood, Jan. 15, 2001, vol. 97, No. 2 ,pp. 426–434.*
Morrison et al., "The Biology of Hematopoietic Stem Cells" Annu. Rev. Cell Dev. Biol. 11:35–71 (1995).
Chen et al., "Delineation of the human hematolymphoid system: potential applications of defined cell populations in cellular thereapy" Immunological Reviews 157:41–51 (1997).
Goodell et al. "CD34+ or DC34–: Does it Really Matter?" Blood 94:2545–47 (1999).
Huang et al., "Symmetry of Initial Cell Divisions Among Primitive Hematopoietic Progenitors is Independent of Ontogenic Age and Regulatory Molecules" Blood 94:2595–2604 (1999).
Vaziri et al. "Evidence for a mitotic clock in human hematopoietic stem cells: Loss of telomeric DNA with age" Proc. Natl. Acad. Sci. 91:9857–60 (1994).
Lansdorp et al., "Developmental changes in the function of hematopoietic stem cells" Experimental Hematology 23:187–191 (1995).
Van der Loo et al., "Marrow– and Spleen–Seeding Efficiencies of All Murine Hematopoietic Stem Cell Subsets Are Decreased by Preincubation with Hematopoietic Growth Factors" Blood 85:2598–2606 (1995).
Peters et al., "Murine Marrow Cells expanded in culture with IL–3, IL–6, IL–11, and SCF acquire an engraftment defect in normal hosts" Experimental Hematology 23:461–469 (1995).
Peters et al., "Ex Vivo Expansion of Murine Marrow Cells with Interleukin–3 (IL–3), IL–6, IL–11, and Stem Cell Factor Leads to Impaired Engraftment in Irradiated Hosts", Blood 87:30–37 (1996).
Yonemura et al., "Interleukin 3 or interleukin 1 abrogates the reconstituting ability of hematopoietic stem cells" Proc. Natl. Acad. Sci. 93:4040–44 (Apr. 1996).
Hoffman et al., "Progress in the development of systems for in vitro expansion of human hematopoietic stem cells" Current Opinion in hematology 184–191 (1999).
Zon et al., "Developmental Biology of Hematopoiesis" Blood 86:2876–2891 (1995).
Lewis "A gene complex controlling segmentation in Drosophila" Nature 276:565–70 (1978).
Tabara et al., "The rde–1 Gene, RNA Interference, and Transposon Silencing in C elegans" Cell 99:123–32 (1999).
Sidow et al., "Diversification of the Wnt gene family on the ancestral lineage of vertegrates" Proc. Natl. Acad. Sci. 89:5098–5102 (1992).
Austin et al., "A Role for the Wnt Gene Family in Hematopoiesis: Expansion of Multilineage Progenitor Cells" Blood 89:3624–3635 (1997).
Nusslein–Volhard et al., "Mutations affecting segment number and polarity in Drosophila" Nature 287:795–810 (1980).
Lin et al., "Germline Stem cell Division and Egg Chamber Development in Transplanted Drosophila Germaria" Developmental Biology 159:140–152 (1993).
Lin et al., "A Novel group of pumillo mutations affects the asymmetric division of germline stem cells in the Drosophila ovary" Development 124:2463–76 (1997).
Lin et al., "The self–renewing mechanism of stem cells in the germline" Curr Opin Cell Biol. 687–693 (1993).
Cox et al., "A Novel class of evolutionarily conserved genes defined by piwi are essential for stem cell self–renewel" Genes & development 12:3715–3727 (1998).
Lin et al., "The tao of stem cells in the germline" Ann. Rev. of Genet. 455–491 (1999).

(Continued)

*Primary Examiner*—Terry McKelvey
(74) *Attorney, Agent, or Firm*—McDonnell Boehnen Hulbert & Berghoff LLP

(57) ABSTRACT

The present invention relates to novel human hiwi protein and genes that encode such proteins. The invention is directed toward the isolation and characterization of human hiwi proteins. The invention specifically provides isolated complementary DNA copies of mRNA corresponding a human hiwi gene. Also provided are recombinant expression constructs capable of expressing the human hiwi gene of the invention in cultures of transformed prokaryotic and eukaryotic cells, as well as such cultures of transformed cells that synthesize the human hiwi proteins encoded therein. The invention also provides methods for isolating human hematopoietic stem cells.

6 Claims, 13 Drawing Sheets

OTHER PUBLICATIONS

Benfey et al., "Stem cells: A tale of two kingdoms" Curr. Biol. 9:171–172 (1999).

King et al., "Somatic signaling mediated by fs(1)Yb is essential for germline stem cell maintenance during drosophila oogenesis" Development 126:1833–44 (1999).

Labow et al., "Conversion of the lac Repressor into an Allosterically Regulated Transcriptional Activator for Mammalian Cells" Mol. Cell. Biol. 10:3343–56 (1990).

Thomas and Capecchi, "Site–Directed Mutagenesis by Gene Targeting in Mouse Embryo–Derived Stem Cells" Cell 51:503–512 (1987).

Bertling et al., "Transfection of a DNA/Protein Complex into Nuclei of Mammalian Cells Using Polyoma Capsids and Electroporation" Bioscience Reports 7:107–112 (1987).

Smithies et al., "Insertion of DNA sequences into the human chromosomal β–globin locus by homologous recombination" Nature 317:230–234 (1985).

Ando et al. "Regulation of G1/S transition by cyclins D2 and D3 in hematopoietic cells" Proc. Natl. Acad. Sci. 90:9571–75 (1993).

Abkowitz et al., "Evidence that hematopoiesis may be a stochastic process in vivo" Nature Medicine 2:190–197 (1996).

Uchida et al. "Primitive Human Hematopoietic Cells Displaying Differential Efflux of the Rhodamine 123 Dye have Distinct Biological Activities" Blood 88:1297–1305 (1996).

Morrison et al., "Cyclophosphamide/granulocyte colony–stimulating factor induces hematopoietic stem cells to proliferate prior to mobilization" Proc. Natl. Acad. Sci. 94:1908–1913 (1997).

Cheshier et al., "In vivo proliferation and cell cycle kinetics of long–term self–renewing hematopoietic stem cells" Proc. Natl. Acad. Sci. 96:3120–25 (1999).

Akazawa et al., "Molecular Characterization of a Rat Negative Regulator with a Basic Helix–Loop–Helix Structure Predominantly Expressed in the Developing Nervous System" Journ of Biol. Chemistry 267:21879–85 (1992).

Bradford et al., "Quiescence cycling, and turnover in the primitive hematopoietic stem cell compartment" Exp. Hematol. 25:445–453 (1997).

Postigo et al., "ZEB, a vertebrae homolog of Drosophila Zfh–1, is a negative regulator of muscle differentiation" 16:3935–43 (1997).

Cox et al., "piwi encodes a nucleoplasmic factor whose activity modulates the number and division rate of germline stem cells" Development 503–514 (2000).

Cox et al., "A novel class of evolutionarily conserved genes defined by piwi are essential for stem cell self–renewal" Genes & Develp. 12:3715–27 (1998).

Davis et al., "Porcine Brain Microvascular Endothelial Cells Support the In Vitro Expansion of Human Primitive Hematopoietic Bone Marrow Progenitor Cells with a High Relating Potential:Requirement for Cell–to–Cell Interactions and Colony–Stimulating Factors" Blood 85:1751–61 (1995).

Terstappen et al., "Sequential Generations of Hematopoietic Colonies Derived From Single Nonlineage–Committed CD34+CD38– Progenitor Cells" Blood 77:1218–1227 (1991).

Bazil et al., "Apoptosis of Human Hematopoietic Progenitor Cells Induced by Crosslinking of Surface CD43, the Major Sialoglycoprotein of Leukocytes" Blood 86:502–511 (1995).

Gluzman et al., "SV40–Transformed Simian Cells Support the Replication of Early SV40 Mutants" Cell 23:175–182 (1981).

Pittenger et al., "Multilineage Potential of Adult Human Mesenchymal Stem Cells" Science 284:143–147 (1999).

Dexter et al., "Conditions Controlling the Proliferation of Haemopoietic Stem Cells in Vitro" J. Cell. Physiol. 91:335–344 (1977).

Wineman et al. "Functional Heterogeneity of the Hematopoietic Microenvironment: Rare Stromal Elements Maintain Long–term Repopulating Stem Cells" Blood 87:4082–90 (1996).

Chenchik et al., "Full–Length cDNA Cloning and Detemination of mRNA 5' and 3' Ends by Amplification of Adaptor–Ligated cDNA" Biotechniques 21:526–534 (1996).

* cited by examiner

```
   1 atgatctttg gtgtgaacac aaggcagaac ttagaccatg ttaaagaatc aaaaacaggt
  61 tcttcaggca ttatagtaag gttaagcact aaccatttcc ggctgacatc ccgtccccag
 121 tgggccttat atcagtatca cattgactat aacccactga tggaagccag aagactccgt
 181 tcagctcttc tttttcaaca cgaagatcta attggaaagt gtcatgcttt tgatggaacg
 241 atattatttt tacctaaaag actacagcaa aaggttactg aagtttttag taagacccgg
 301 aatggagagg atgtgaggat aacgatcact ttaacaaatg aacttccacc tacatcacca
 361 acttgtttgc agttctataa tattattttc aggaggcttt tgaaaatcat gaatttgcaa
 421 caaattggac gaaattatta taacccaaat gacccaattg atattccaag tcacaggttg
 481 gtgatttggc ctggcttcac tacttccatc cttcagtatg aaaacagcat catgctctgc
 541 actgacgtta gccataaagt ccttcgaagt gagactgttt tggatttcat gttcaacttt
 601 tatcatcaga cagaagaaca taaatttcaa gaacaagttt ccaaagaact aataggttta
 661 gttgttctta ccaagtataa caataagaca tacagagtgg atgatattga ctgggaccag
 721 aatcccaaga gcacctttaa gaaagccgac ggctctgaag tcagcttctt agaatactac
 781 aggaagcaat acaaccaaga gatcaccgac ttgaagcagc ctgtcttggt cagccagccc
 841 aagagaaggc ggggccctgg gggacactg ccagggcctg ccatgctcat tcctgagctc
 901 tgctatctta caggtctaac tgataaaatg cgtaatgatt ttaacgtgat gaaagactta
 961 gccgttcata caagactaac tccagagcaa aggcagcgtg aagtgggacg actcattgat
1021 tacattcata aaaacgataa tgttcaaagg gagcttcgag actggggttt gagctttgat
1081 tccaacttac tgtccttctc aggaagaatt ttgcaaacag aaaagattca ccaaggtgga
1141 aaaacatttg attacaatcc acaatttgca gattggtcca agaaacaag aggtgcacca
1201 ttaattagtg ttaagccact agataactgg ctgttgatct atacgcgaag aaattatgaa
1261 gcagccaatt cattgataca aatctatt aaagttacac cagccatggg catgcaaatg
1321 agaaaagcaa taatgattga agtggatgac agaactgaag cctacttaag agtcttacag
1381 caaaaggtca cagcagacac ccagatagtt gtctgtctgt tgtcaagtaa tcggaaggac
1441 aaatacgatg ctattaaaaa atacctgtgt acagattgcc ctaccccaag tcagtgtgtg
1501 gtggcccgaa ccttaggcaa acagcaaact gtcatggcca ttgctacaaa gattgcccta
1561 cagatgaact gcaagatggg aggagagctc tggagggtgg acatccccct gaagctcgtg
1621 atgatcgttg gcatcgattg ttaccatgac atgacagctg gcggaggtc aatcgcagga
1681 tttgttgcca gcatcaatga agggatgacc cgctggttct cacgctgcat atttcaggat
1741 agaggacagg agctggtaga tgggctcaaa gtctgcctgc aagcggctct gagggcttgg
1801 aatagctgca atgagtacat gcccagccgg atcatcgtgt accgcgatgg cgtaggagac
1861 ggccagctga aaacactggt gaactacgaa gtgccacagt ttttggattg tctaaaatcc
1921 attggtagag gttacaaccc tagactaacg gtaattgtgg tgaagaaaag agtgaacacc
1981 agattttttg ctcagtctgg aggaagactt cagaatccac ttcctggaac agttattgat
2041 gtagaggtta ccagaccaga atggtatgac ttttttatcg tgagccaggc tgtgagaagt
2101 ggtagtgttt ctcccacaca ttacaatgtc atctatgaca acagcggcct gaagccagac
2161 cacatacagc gcttgaccta caagctgtgc cacatctatt acaactggcc aggtgtcatt
2221 cgtgttcctg ctccttgcca gtacgccac aagctggctt ttcttgttgg ccagagtatt
2281 cacagagagc caaatctgtc actgtcaaac cgcctttact acctctaa
```

Figure 1

```
Met Ile Phe Gly Val Asn Thr Arg Gln Asn Leu Asp His Val Lys Glu Ser Lys Thr Gly Ser Ser Gly Ile Ile Val Arg Leu Ser Thr    30
Asn His Phe Arg Leu Thr Ser Arg Pro Gln Trp Ala Leu Tyr Gln Tyr His Ile Asp Tyr Asn Pro Leu Met Glu Ala Arg Arg Leu Arg     60
Ser Ala Leu Leu Phe Gln His Glu Asp Leu Ile Gly Lys Cys His Ala Phe Asp Gly Thr Ile Leu Phe Leu Pro Lys Arg Leu Gln Gln     90
Lys Val Thr Gln Val Phe Ser Lys Thr Arg Asn Gly Glu Asp Val Arg Ile Thr Ile Thr Leu Thr Asn Glu Leu Pro Pro Thr Ser Pro    120
Thr Cys Leu Gln Phe Tyr Asn Ile Ile Phe Arg Arg Leu Leu Lys Ile Met Asn Leu Gln Gln Ile Gly Arg Asn Tyr Tyr Asn Pro Asn    150
Asp Pro Ile Asp Ile Pro Ser His Arg Leu Val Ile Trp Pro Gly Phe Thr Thr Ser Ile Leu Gln Tyr Glu Asn Ser Ile Met Leu Cys    180
Thr Asp Val Ser His Lys Val Leu Arg Ser Glu Thr Val Leu Asp Phe Met Phe Asn Phe Tyr His Gln Thr Glu His Lys Phe Gln        210
Glu Gln Val Ser Lys Glu Leu Ile Gly Leu Val Val Leu Thr Lys Asn Asn Lys Thr Tyr Arg Val Asp Asp Ile Asp Trp Asp Gln        240
Asn Pro Lys Ser Thr Phe Lys Ala Asp Gly Ser Val Ser Phe Leu Glu Tyr Tyr Arg Lys Gln Tyr Asn Gln Gly Ile Thr Asp            270
Leu Lys Gln Pro Val Leu Val Ser Gln Pro Lys Arg Arg Arg Gly Pro Gly Thr Leu Pro Gly Pro Ala Met Leu Ile Pro Glu Leu        300
Cys Tyr Leu Thr Gly Leu Thr Asp Lys Met Arg Asn Asp Phe Asn Val Met Lys Asp Leu Ala Val His Thr Arg Leu Thr Pro Glu Gln   330
Arg Gln Arg Glu Val Gly Arg Leu Ile Asp Tyr Ile His Lys Asn Asp Asn Val Gln Arg Glu Leu Arg Asp Trp Gly Leu Ser Phe Asp   360
Ser Asn Leu Leu Ser Phe Ser Gly Arg Ile Leu Gln Thr Glu Leu Lys Ile His Gln Gly Gly Lys Thr Phe Asp Tyr Asn Pro Gln Phe Ala 390
Asp Trp Ser Lys Glu Thr Arg Gly Ala Pro Leu Ile Ser Val Lys Pro Leu Asp Asn Trp Leu Leu Ile Tyr Thr Arg Arg Asn Tyr Glu    420
Ala Ala Asn Ser Leu Ile Gln Asn Leu Phe Lys Val Thr Pro Ala Met Gly Met Gln Met Arg Lys Ala Ile Met Ile Glu Val Asp Asp    450
Arg Thr Glu Ala Tyr Leu Arg Val Leu Gln Gln Lys Val Thr Ala Asp Thr Gln Ile Val Val Cys Leu Leu Ser Ser Asn Arg Lys Asp    480
Lys Tyr Asp Ala Ile Lys Lys Tyr Leu Cys Thr Asp Cys Pro Thr Pro Ser Gln Cys Val Val Ala Arg Thr Leu Gly Lys Gln Gln Thr    510
```

Figure 1
Continued

Val Met Ala Ile Ala Thr Lys Ile Ala Leu Gln Met Asn Cys Lys Met Gly Gly Glu Leu Trp Arg Val Asp Ile Pro Leu Lys Leu Val   540

Met Ile Val Gly Ile Asp Cys Tyr His Asp Met Thr Ala Gly Arg Arg Ser Ile Ala Gly Phe Val Ala Ser Ile Asn Glu Gly Met Thr   570

Arg Trp Phe Ser Arg Cys Ile Phe Gln Asp Arg Gly Gln Glu Leu Val Asp Gly Leu Lys Val Cys Leu Gln Ala Ala Leu Arg Ala Trp   600

Asn Ser Cys Asn Glu Tyr Met Pro Ser Arg Ile Ile Val Tyr Arg Asp Gly Val Gly Asp Gly Gln Leu Lys Thr Leu Val Asn Tyr Glu   630

Val Pro Gln Phe Leu Asp Cys Leu Lys Ser Ile Gly Arg Gly Tyr Asn Pro Arg Leu Thr Val Ile Val Val Lys Arg Val Asn Thr   660

Arg Phe Phe Ala Gln Ser Gly Gly Arg Leu Gln Asn Pro Leu Pro Gly Thr Val Ile Asp Val Glu Val Thr Arg Pro Glu Trp Tyr Asp   690

Phe Phe Ile Val Ser Gln Ala Val Arg Ser Gly Ser Val Ser Pro Thr His Tyr Asn Val Ile Tyr Asp Asn Ser Gly Leu Lys Pro Asp   720

His Ile Gln Arg Leu Thr Tyr Lys Leu Cys His Ile Tyr Tyr Asn Trp Pro Gly Val Ile Arg Val Pro Ala Pro Cys Gln Tyr Ala His   750

Lys Leu Ala Phe Leu Val Gly Gln Ser Ile His Arg Glu Pro Asn Leu Ser Leu Ser Asn Arg Leu Tyr Tyr Leu   775

Figure 1
Continued

```
PIWI  MADDQGRGRRRPLNEDDSSTSRGSGDGPRVKVFRGSSSGDPRADPRIEASRERRALEEAPR
      M                             F    G          R   L           61
HIWI  M------------------------IF-----G----------VNTRQNLDHV--

PIWI  REGGPPERKPWGDQYDYLNTRPVELVSKKGTDGVPVMLQTNFFRLKTKPEWRIVHYHVEFE
                K             E   SK G+  G+  V L TN FRL ++P+W +  YH+++  122
HIWI  --------K--------------E--SKTGSSGIIVRLSTNHFRLTSRPQWALYQYHIDYN

PIWI  PSIENPRVRMGVLSNHANLLGSGYLFDGLQLFTTRKFEQEITVLSGKSKLDIEYKISIKFV
      P  +E  R+R   +L  H +L+G   + FDG  LF   ++ +Q++T +    K++    + +I+I  183
HIWI  PLMEARRLRSALLFQHEDLIGKCHAFDGTILFLPKRLQQKVTEVFSKTRNGEDVRITITLT

PIWI  GFISCAEPRFLQVLNLILRRSMKGLNLELVGRNLFDPRAKIEIREFKMELWPGYETSIRQH
          +      P  LQ   N+I  RR  +K  +NL+  +GRN  ++P    I+I    ++ +WPG+ TSI  Q+  244
HIWI  NELPPTSPTCLQFYNIIFRRLLKIMNLQQIGRNYYNPNDPIDIPSHRLVIWPGFTTSILQY

PIWI  EKDILLGTEITHKVMRTETIYDIMRRCSHNPARH--QDEVRVNVLDLIVLTDYNNRTYRIN
      E   I+L  T+++HKV+R+ET+  D M     H        H    Q++V       ++ L+VLT YNN+TYR++  305
HIWI  ENSIMLCTDVSHKVLRSETVLDFMFNFYHQTEEHKFQEQVSKELIGLVVLTKYNNKTYRVD

PIWI  DVDPGQTPKSTF-SCKGRDISFVEYYLTKYNIRIRDHNQPLLISK-NRDKALKTNASELVV
      D+D+   Q PKSTF      G ++SF+EYY  +YN    I D   QP+L+S+    R +                + 366
HIWI  DIDWDQNPKSTFKKADGSEVSFLEYYRKQYNQEITDLKQPVLVSQPKRRRGPGGTLPGPAM

PIWI  LIPELCRVTGLNAEMRSNFQLMRAMSSYTRMNPKQR---TDRLRAFNHRLQNTPESVKVLR
      LIPELC  +TGL   +MR++F  +M+  ++    +TR+  P+QR           RL    + H+  N              LR  427
HIWI  LIPELCYLTGLTDKMRNDFNVMKDLAVHTRLTPEQRQREVGRLIDYIHKNDNVQ---RELR

PIWI  DWNMELDKNVTEVQGRIIGQQNIVPHNGKVPAGEN---ADWQRHFRDQRMLTTPSDGLDRW
      DW +   D N+        GRI+    + I   H G          N     ADW +  R     +++          LD W 488
HIWI  DWGLSFDSNLLSFSGRILQTEKI--HQGGKTFDYNPQFADWSKETRGAPLISVKP--LDNW

PIWI  AVIAPQRNSHELRTLLDSLYRAASGMGLRIRSPQEFIIYDDRTGTYVRAMDDCVRSDPKLI
        +I   +RN          +L+    +L++        MG+++R      I    DDRT   Y+R   +   V  +D++++ 549
HIWI  LLIYTRRNYEAANSLIQNLFKVTPAMGMQMRK-AIMIEVDDRTEAYLRVLQQKVTADTQIV

PIWI  LCLVPNDNAERYSSIKKRGYVDRAVPTQVVTLKTTKKPYSLMSIATKIAIQLNCKLGYTPW
         CL+  ++   ++Y  +IKK       D     P+Q V   +T  K   ++M+IATKIA+Q+NCK+G            W 610
HIWI  VCLLSSNRKDKYDAIKKYLCTDCPTPSQCVVARTLGKQQTVMAIATKIALQMNCKMGGELW

PIWI  MIELPLSGLMTIGFDIAKSTRDRKRAYGALIASMDLQQNSTYFSTVTECSAFDVLANTLWP
        +++PL  +M  +G  D            +R+       +AS++  +    +   +FS           L+   L   671
HIWI  RVDIPLKLVMIVGIDCYHDMTAGRRSIAGFVASIN-EGMTRWFSRCIFQDRGQELVDGLKV

PIWI  MIAKALRQYQHEHRKLPSRIVFYRDGVSSGSLKQLFEFEVKDIIEKLKTEYARVQLSPPQL
         +  ALR +     +   +PSRI+ YRDGV  G LK L   +EV    ++ LK+                    P+L 732
HIWI  CLQAALRAWNSCNEYMPSRIIVYRDGVGDGQLKTLVNYEVPQFLDCLKSIGRGYN---PRL

PIWI  AYIVVTRSMNTRFFLNG----QNPPPGTIVDDVITLPERYDFYLVSQQVRQGTVSPTSYNV
         IVV +  +NTRFF           QNP PGT++D   +T PE YDF++VSQ VR G+VSPT YNV 793
HIWI  TVIVVKKRVNTRFFAQSGGRLQNPLPGTVIDVEVTRPEWYDFFIVSQAVRSGSVSPTHYNV

PIWI  LYSSMGLSPEKMQKLTYKMCHLYYNWSGTTRVPAVCQYAKKLATLVGTNLHSIPQNALEK
       +Y +  GL P+  +Q+LTYK+CH+YYNW G   RVPA CQYA  KLA  LVG ++H   P   +L 854
HIWI  IYDNSGLKPDHIQRLTYKLCHIYYNWPGVIRVPAPCQYAHKLAFLVGQSIHREPNLSLSN

PIWI  KFYYL
      +  YYL  859
HIWI  RLYYL
```

Figure 1
Continued

SEQUENCE LISTING

```
<160> NUMBER OF SEQ ID NOS: 17
<210> SEQ ID NO 1
<211> LENGTH: 2328
<212> TYPE: DNA
<213> ORGANISM: Homo sapiens
<220> FEATURE:
<221> NAME/KEY: CDS
<222> LOCATION: (1)..(2328)
<223> OTHER INFORMATION: Human Hiwi Protein

<400> SEQUENCE: 1 atg atc ttt ggt gtg aac aca agg cag aac tta gac cat gtt aaa gaa      48
Met Ile Phe Gly Val Asn Thr Arg Gln Asn Leu Asp His Val Lys Glu
1               5                   10                  15 tca aaa aca ggt tct tca ggc att ata gta agg tta agc act aac cat      96
Ser Lys Thr Gly Ser Ser Gly Ile Ile Val Arg Leu Ser Thr Asn His
            20                  25                  30 ttc cgg ctg aca tcc cgt ccc cag tgg gcc tta tat cag tat cac att     144
Phe Arg Leu Thr Ser Arg Pro Gln Trp Ala Leu Tyr Gln Tyr His Ile
        35                  40                  45 gac tat aac cca ctg atg gaa gcc aga aga ctc cgt tca gct ctt ctt     192
Asp Tyr Asn Pro Leu Met Glu Ala Arg Arg Leu Arg Ser Ala Leu Leu
    50                  55                  60 ttt caa cac gaa gat cta att gga aag tgt cat gct ttt gat gga acg     240
Phe Gln His Glu Asp Leu Ile Gly Lys Cys His Ala Phe Asp Gly Thr
65                  70                  75                  80 ata tta ttt tta cct aaa aga cta cag caa aag gtt act gaa gtt ttt     288
Ile Leu Phe Leu Pro Lys Arg Leu Gln Gln Lys Val Thr Glu Val Phe
                85                  90                  95 agt aag acc cgg aat gga gag gat gtg agg ata acg atc act tta aca     336
Ser Lys Thr Arg Asn Gly Glu Asp Val Arg Ile Thr Ile Thr Leu Thr
            100                 105                 110 aat gaa ctt cca cct aca tca cca act tgt ttg cag ttc tat aat att     384
Asn Glu Leu Pro Pro Thr Ser Pro Thr Cys Leu Gln Phe Tyr Asn Ile
        115                 120                 125 att ttc agg agg ctt ttg aaa atc atg aat tta caa caa att gga cga     432
Ile Phe Arg Arg Leu Leu Lys Ile Met Asn Leu Gln Gln Ile Gly Arg
    130                 135                 140
```

```
                                        -continued aat tat tat aac cca aat gac cca att gat att cca agt cac agg ttg      480
Asn Tyr Tyr Asn Pro Asn Asp Pro Ile Asp Ile Pro Ser His Arg Leu
145             150                 155                 160 gtg att tgg cct ggc ttc act act tcc atc ctt cag tat gaa aac agc      528
Val Ile Trp Pro Gly Phe Thr Thr Ser Ile Leu Gln Tyr Glu Asn Ser
                165                 170                 175 atc atg ctc tgc act gac gtt agc cat aaa gtc ctt cga agt gag act      576
Ile Met Leu Cys Thr Asp Val Ser His Lys Val Leu Arg Ser Glu Thr
            180                 185                 190 gtt ttg gat ttc atg ttc aac ttt tat cat cag aca gaa gaa cat aaa      624
Val Leu Asp Phe Met Phe Asn Phe Tyr His Gln Thr Glu Glu His Lys
        195                 200                 205 ttt caa gaa caa gtt tcc aaa gaa cta ata ggt tta gtt gtt ctt acc      672
Phe Gln Glu Gln Val Ser Lys Glu Leu Ile Gly Leu Val Val Leu Thr
    210                 215                 220 aag tat aac aat aag aca tac aga gtg gat gat att gac tgg gac cag      720
Lys Tyr Asn Asn Lys Thr Tyr Arg Val Asp Asp Ile Asp Trp Asp Gln
225             230                 235                 240 aat ccc aag agc acc ttt aag aaa gcc gac ggc tct gaa gtc agc ttc      768
Asn Pro Lys Ser Thr Phe Lys Lys Ala Asp Gly Ser Glu Val Ser Phe
                245                 250                 255 tta gaa tac tac agg aag caa tac aac caa gag atc acc gac ttg aag      816
Leu Glu Tyr Tyr Arg Lys Gln Tyr Asn Gln Glu Ile Thr Asp Leu Lys
            260                 265                 270 cag cct gtc ttg gtc agc cag ccc aag aga agg cgg ggc cct ggg ggg      864
Gln Pro Val Leu Val Ser Gln Pro Lys Arg Arg Arg Gly Pro Gly Gly
        275                 280                 285 aca ctg cca ggg cct gcc atg ctc att cct gag ctc tgc tat ctt aca      912
Thr Leu Pro Gly Pro Ala Met Leu Ile Pro Glu Leu Cys Tyr Leu Thr
    290                 295                 300 ggt cta act gat aaa atg cgt aat gat ttt aac gtg atg aaa gac tta      960
Gly Leu Thr Asp Lys Met Arg Asn Asp Phe Asn Val Met Lys Asp Leu
305             310                 315                 320 gcc gtt cat aca aga cta act cca gag caa agg cag cgt gaa gtg gga     1008
Ala Val His Thr Arg Leu Thr Pro Glu Gln Arg Gln Arg Glu Val Gly
                325                 330                 335 cga ctc att gat tac att cat aaa aac gat aat gtt caa agg gag ctt     1056
Arg Leu Ile Asp Tyr Ile His Lys Asn Asp Asn Val Gln Arg Glu Leu
            340                 345                 350 cga gac tgg ggt ttg agc ttt gat tcc aac tta ctg tcc ttc tca gga     1104
Arg Asp Trp Gly Leu Ser Phe Asp Ser Asn Leu Leu Ser Phe Ser Gly
        355                 360                 365 aga att ttg caa aca gaa aag att cac caa ggt gga aaa aca ttt gat     1152
Arg Ile Leu Gln Thr Glu Lys Ile His Gln Gly Gly Lys Thr Phe Asp
    370                 375                 380 tac aat cca caa ttt gca gat tgg tcc aaa gaa aca aga ggt gca cca     1200
Tyr Asn Pro Gln Phe Ala Asp Trp Ser Lys Glu Thr Arg Gly Ala Pro
385             390                 395                 400 tta att agt gtt aag cca cta gat aac tgg ctg ttg atc tat acg cga     1248
Leu Ile Ser Val Lys Pro Leu Asp Asn Trp Leu Leu Ile Tyr Thr Arg
                405                 410                 415 aga aat tat gaa gca gcc aat tca ttg ata caa aat cta ttt aaa gtt     1296
Arg Asn Tyr Glu Ala Ala Asn Ser Leu Ile Gln Asn Leu Phe Lys Val
            420                 425                 430 aca cca gcc atg ggc atg caa atg aga aaa gca ata atg att gaa gtg     1344
Thr Pro Ala Met Gly Met Gln Met Arg Lys Ala Ile Met Ile Glu Val
        435                 440                 445 gat gac aga act gaa gcc tac tta aga gtc tta cag caa aag gtc aca     1392
Asp Asp Arg Thr Glu Ala Tyr Leu Arg Val Leu Gln Gln Lys Val Thr
    450                 455                 460
```

```
gca gac acc cag ata gtt gtc tgt ctg ttg tca agt aat cgg aag gac      1440
Ala Asp Thr Gln Ile Val Val Cys Leu Leu Ser Ser Asn Arg Lys Asp
465                 470                 475                 480 aaa tac gat gct att aaa aaa tac ctg tgt aca gat tgc cct acc cca      1488
Lys Tyr Asp Ala Ile Lys Lys Tyr Leu Cys Thr Asp Cys Pro Thr Pro
                    485                 490                 495 agt cag tgt gtg gtg gcc cga acc tta ggc aaa cag caa act gtc atg      1536
Ser Gln Cys Val Val Ala Arg Thr Leu Gly Lys Gln Gln Thr Val Met
500                 505                 510 gcc att gct aca aag att gcc cta cag atg aac tgc aag atg gga gga      1584
Ala Ile Ala Thr Lys Ile Ala Leu Gln Met Asn Cys Lys Met Gly Gly
        515                 520                 525 gag ctc tgg agg gtg gac atc ccc ctg aag ctc gtg atg atc gtt ggc      1632
Glu Leu Trp Arg Val Asp Ile Pro Leu Lys Leu Val Met Ile Val Gly
530                 535                 540 atc gat tgt tac cat gac atg aca gct ggg cgg agg tca atc gca gga      1680
Ile Asp Cys Tyr His Asp Met Thr Ala Gly Arg Arg Ser Ile Ala Gly
545                 550                 555                 560 ttt gtt gcc agc atc aat gaa ggg atg acc cgc tgg ttc tca cgc tgc      1728
Phe Val Ala Ser Ile Asn Glu Gly Met Thr Arg Trp Phe Ser Arg Cys
                565                 570                 575 ata ttt cag gat aga gga cag gag ctg gta gat ggg ctc aaa gtc tgc      1776
Ile Phe Gln Asp Arg Gly Gln Glu Leu Val Asp Gly Leu Lys Val Cys
                    580                 585                 590 ctg caa gcg gct ctg agg gct tgg aat agc tgc aat gag tac atg ccc      1824
Leu Gln Ala Ala Leu Arg Ala Trp Asn Ser Cys Asn Glu Tyr Met Pro
            595                 600                 605 agc cgg atc atc gtg tac cgc gat ggc gta gga gac ggc cag ctg aaa      1872
Ser Arg Ile Ile Val Tyr Arg Asp Gly Val Gly Asp Gly Gln Leu Lys
610                 615                 620 aca ctg gtg aac tac gaa gtg cca cag ttt ttg gat tgt cta aaa tcc      1920
Thr Leu Val Asn Tyr Glu Val Pro Gln Phe Leu Asp Cys Leu Lys Ser
625                 630                 635                 640 att ggt aga ggt tac aac cct aga cta acg gta att gtg gtg aag aaa      1968
Ile Gly Arg Gly Tyr Asn Pro Arg Leu Thr Val Ile Val Val Lys Lys
                645                 650                 655 aga gtg aac acc aga ttt ttt gct cag tct gga gga aga ctt cag aat      2016
Arg Val Asn Thr Arg Phe Phe Ala Gln Ser Gly Gly Arg Leu Gln Asn
                    660                 665                 670 cca ctt cct gga aca gtt att gat gta gag gtt acc aga cca gaa tgg      2064
Pro Leu Pro Gly Thr Val Ile Asp Val Glu Val Thr Arg Pro Glu Trp
            675                 680                 685 tat gac ttt ttt atc gtg agc cag gct gtg aga agt ggt agt gtt tct      2112
Tyr Asp Phe Phe Ile Val Ser Gln Ala Val Arg Ser Gly Ser Val Ser
690                 695                 700 ccc aca cat tac aat gtc atc tat gac aac agc ggc ctg aag cca gac      2160
Pro Thr His Tyr Asn Val Ile Tyr Asp Asn Ser Gly Leu Lys Pro Asp
705                 710                 715                 720 cac ata cag cgc ttg acc tac aag ctg tgc cac atc tat tac aac tgg      2208
His Ile Gln Arg Leu Thr Tyr Lys Leu Cys His Ile Tyr Tyr Asn Trp
                725                 730                 735 cca ggt gtc att cgt gtt cct gct cct tgc cag tac gcc cac aag ctg      2256
Pro Gly Val Ile Arg Val Pro Ala Pro Cys Gln Tyr Ala His Lys Leu
                    740                 745                 750 gct ttt ctt gtt ggc cag agt att cac aga gag cca aat ctg tca ctg      2304
Ala Phe Leu Val Gly Gln Ser Ile His Arg Glu Pro Asn Leu Ser Leu
            755                 760                 765 tca aac cgc ctt tac tac ctc taa                                      2328
Ser Asn Arg Leu Tyr Tyr Leu
```

-continued

```
        770             775

<210> SEQ ID NO 2
<211> LENGTH: 775
<212> TYPE: PRT
<213> ORGANISM: Homo sapiens

<400> SEQUENCE: 2

Met Ile Phe Gly Val Asn Thr Arg Gln Asn Leu Asp His Val Lys Glu
1               5                   10                  15

Ser Lys Thr Gly Ser Ser Gly Ile Ile Val Arg Leu Ser Thr Asn His
            20                  25                  30

Phe Arg Leu Thr Ser Arg Pro Gln Trp Ala Leu Tyr Gln Tyr His Ile
        35                  40                  45

Asp Tyr Asn Pro Leu Met Glu Ala Arg Arg Leu Arg Ser Ala Leu Leu
    50                  55                  60

Phe Gln His Glu Asp Leu Ile Gly Lys Cys His Ala Phe Asp Gly Thr
65                  70                  75                  80

Ile Leu Phe Leu Pro Lys Arg Leu Gln Gln Lys Val Thr Glu Val Phe
                85                  90                  95

Ser Lys Thr Arg Asn Gly Glu Asp Val Arg Ile Thr Ile Thr Leu Thr
            100                 105                 110

Asn Glu Leu Pro Pro Thr Ser Pro Thr Cys Leu Gln Phe Tyr Asn Ile
        115                 120                 125

Ile Phe Arg Arg Leu Leu Lys Ile Met Asn Leu Gln Gln Ile Gly Arg
    130                 135                 140

Asn Tyr Tyr Asn Pro Asn Asp Pro Ile Asp Ile Pro Ser His Arg Leu
145                 150                 155                 160

Val Ile Trp Pro Gly Phe Thr Thr Ser Ile Leu Gln Tyr Glu Asn Ser
                165                 170                 175

Ile Met Leu Cys Thr Asp Val Ser His Lys Val Leu Arg Ser Glu Thr
            180                 185                 190

Val Leu Asp Phe Met Phe Asn Phe Tyr His Gln Thr Glu Glu His Lys
        195                 200                 205

Phe Gln Glu Gln Val Ser Lys Glu Leu Ile Gly Leu Val Leu Thr
    210                 215                 220

Lys Tyr Asn Asn Lys Thr Tyr Arg Val Asp Asp Ile Asp Trp Asp Gln
225                 230                 235                 240

Asn Pro Lys Ser Thr Phe Lys Lys Ala Asp Gly Ser Glu Val Ser Phe
                245                 250                 255

Leu Glu Tyr Tyr Arg Lys Gln Tyr Asn Gln Glu Ile Thr Asp Leu Lys
            260                 265                 270

Gln Pro Val Leu Val Ser Gln Pro Lys Arg Arg Gly Pro Gly Gly
        275                 280                 285

Thr Leu Pro Gly Pro Ala Met Leu Ile Pro Glu Leu Cys Tyr Leu Thr
    290                 295                 300

Gly Leu Thr Asp Lys Met Arg Asn Asp Phe Asn Val Met Lys Asp Leu
305                 310                 315                 320

Ala Val His Thr Arg Leu Thr Pro Glu Gln Arg Gln Arg Glu Val Gly
                325                 330                 335

Arg Leu Ile Asp Tyr Ile His Lys Asn Asp Asn Val Gln Arg Glu Leu
            340                 345                 350

Arg Asp Trp Gly Leu Ser Phe Asp Ser Asn Leu Leu Ser Phe Ser Gly
        355                 360                 365
```

-continued

```
Arg Ile Leu Gln Thr Glu Lys Ile His Gln Gly Gly Lys Thr Phe Asp
        370                 375                 380

Tyr Asn Pro Gln Phe Ala Asp Trp Ser Lys Glu Thr Arg Gly Ala Pro
385                     390                 395                 400

Leu Ile Ser Val Lys Pro Leu Asp Asn Trp Leu Leu Ile Tyr Thr Arg
                405                 410                 415

Arg Asn Tyr Glu Ala Ala Asn Ser Leu Ile Gln Asn Leu Phe Lys Val
            420                 425                 430

Thr Pro Ala Met Gly Met Gln Met Arg Lys Ala Ile Met Ile Glu Val
                435                 440                 445

Asp Asp Arg Thr Glu Ala Tyr Leu Arg Val Leu Gln Gln Lys Val Thr
        450                 455                 460

Ala Asp Thr Gln Ile Val Val Cys Leu Leu Ser Ser Asn Arg Lys Asp
465                 470                 475                 480

Lys Tyr Asp Ala Ile Lys Lys Tyr Leu Cys Thr Asp Cys Pro Thr Pro
                485                 490                 495

Ser Gln Cys Val Val Ala Arg Thr Leu Gly Lys Gln Gln Thr Val Met
            500                 505                 510

Ala Ile Ala Thr Lys Ile Ala Leu Gln Met Asn Cys Lys Met Gly Gly
                515                 520                 525

Glu Leu Trp Arg Val Asp Ile Pro Leu Lys Leu Val Met Ile Val Gly
        530                 535                 540

Ile Asp Cys Tyr His Asp Met Thr Ala Gly Arg Arg Ser Ile Ala Gly
545                 550                 555                 560

Phe Val Ala Ser Ile Asn Glu Gly Met Thr Arg Trp Phe Ser Arg Cys
                565                 570                 575

Ile Phe Gln Asp Arg Gly Gln Glu Leu Val Asp Gly Leu Lys Val Cys
            580                 585                 590

Leu Gln Ala Ala Leu Arg Ala Trp Asn Ser Cys Asn Glu Tyr Met Pro
        595                 600                 605

Ser Arg Ile Ile Val Tyr Arg Asp Gly Val Gly Asp Gly Gln Leu Lys
        610                 615                 620

Thr Leu Val Asn Tyr Glu Val Pro Gln Phe Leu Asp Cys Leu Lys Ser
625                 630                 635                 640

Ile Gly Arg Gly Tyr Asn Pro Arg Leu Thr Val Ile Val Val Lys Lys
                645                 650                 655

Arg Val Asn Thr Arg Phe Phe Ala Gln Ser Gly Gly Arg Leu Gln Asn
            660                 665                 670

Pro Leu Pro Gly Thr Val Ile Asp Val Glu Val Thr Arg Pro Glu Trp
        675                 680                 685

Tyr Asp Phe Phe Ile Val Ser Gln Ala Val Arg Ser Gly Ser Val Ser
        690                 695                 700

Pro Thr His Tyr Asn Val Ile Tyr Asp Asn Ser Gly Leu Lys Pro Asp
705                 710                 715                 720

His Ile Gln Arg Leu Thr Tyr Lys Leu Cys His Ile Tyr Tyr Asn Trp
                725                 730                 735

Pro Gly Val Ile Arg Val Pro Ala Pro Cys Gln Tyr Ala His Lys Leu
                740                 745                 750

Ala Phe Leu Val Gly Gln Ser Ile His Arg Glu Pro Asn Leu Ser Leu
            755                 760                 765

Ser Asn Arg Leu Tyr Tyr Leu
770                 775
```

<210> SEQ ID NO 3
<211> LENGTH: 24
<212> TYPE: DNA
<213> ORGANISM: Artificial Sequence
<220> FEATURE:
<223> OTHER INFORMATION: Glyceraldehyde phosphate dehydrogenase cDNA for
    ward primer

<400> SEQUENCE: 3
ggctgagaac gggaagcttg tcat                                           24

<210> SEQ ID NO 4
<211> LENGTH: 24
<212> TYPE: DNA
<213> ORGANISM: Artificial Sequence
<220> FEATURE:
<223> OTHER INFORMATION: Glyceraldehyde phosphate dehydrogenase cDNA rev
    erse primer

<400> SEQUENCE: 4
cagccttctc catggtggtg aaga                                           24

<210> SEQ ID NO 5
<211> LENGTH: 20
<212> TYPE: DNA
<213> ORGANISM: Artificial Sequence
<220> FEATURE:
<223> OTHER INFORMATION: B2 microglobulin forward primer

<400> SEQUENCE: 5
ctcgcgctac tctctctttc                                                20

<210> SEQ ID NO 6
<211> LENGTH: 21
<212> TYPE: DNA
<213> ORGANISM: Artificial Sequence
<220> FEATURE:
<223> OTHER INFORMATION: B2 microglobulin reverse primer

<400> SEQUENCE: 6
catgtctcga tcccacttaa c                                              21

<210> SEQ ID NO 7
<211> LENGTH: 22
<212> TYPE: DNA
<213> ORGANISM: Artificial Sequence
<220> FEATURE:
<223> OTHER INFORMATION: CD34 hiwi DNA forward primer

<400> SEQUENCE: 7
gaagcagcct gtcttggtca gc                                             22

<210> SEQ ID NO 8
<211> LENGTH: 25
<212> TYPE: DNA
<213> ORGANISM: Artificial Sequence
<220> FEATURE:
<223> OTHER INFORMATION: CD34 hiwi DNA reverse primer

<400> SEQUENCE: 8
gaatcaaagc tcaaacccca gtctc                                          25

<210> SEQ ID NO 9
<211> LENGTH: 25
<212> TYPE: DNA
<213> ORGANISM: Artificial Sequence
<220> FEATURE:

<223> OTHER INFORMATION: human testis hiwi gene reverse primer

<400> SEQUENCE: 9
cgctgtatgt ggtctggctt caggc                                    25

<210> SEQ ID NO 10
<211> LENGTH: 30
<212> TYPE: DNA
<213> ORGANISM: Artificial Sequence
<220> FEATURE:
<223> OTHER INFORMATION: human testis hiwi gene reverse primer

<400> SEQUENCE: 10
gggagaaaca ctaccacttc tcacagcctg                               30

<210> SEQ ID NO 11
<211> LENGTH: 27
<212> TYPE: DNA
<213> ORGANISM: Artificial Sequence
<220> FEATURE:
<223> OTHER INFORMATION: Marathon Ready Human Testis cDNA Kit AP-1
      primer

<400> SEQUENCE: 11
ccatcctaat acgactcact atagggc                                  27

<210> SEQ ID NO 12
<211> LENGTH: 23
<212> TYPE: DNA
<213> ORGANISM: Artificial Sequence
<220> FEATURE:
<223> OTHER INFORMATION: Marathon Ready Human Testis cDNA Kit AP-2
      primer

<400> SEQUENCE: 12
actcactata gggctcgagc ggc                                      23

<210> SEQ ID NO 13
<211> LENGTH: 844
<212> TYPE: PRT
<213> ORGANISM: Drosophila melanogaster
<220> FEATURE:
<221> NAME/KEY: misc_feature
<223> OTHER INFORMATION: PIWI protein

<400> SEQUENCE: 13

Met Ala Asp Asp Gln Gly Arg Gly Arg Arg Pro Leu Asn Glu Asp
1               5                   10                  15

Asp Ser Ser Thr Ser Arg Gly Ser Gly Asp Gly Pro Arg Val Lys Val
                20                  25                  30

Phe Arg Gly Ser Ser Gly Asp Pro Arg Ala Asp Pro Arg Ile Glu
        35                  40                  45

Ala Ser Arg Glu Arg Arg Ala Leu Glu Glu Ala Pro Arg Arg Glu Gly
    50                  55                  60

Gly Pro Pro Glu Arg Lys Pro Trp Gly Asp Gln Tyr Asp Tyr Leu Asn
65                  70                  75                  80

Thr Arg Pro Val Glu Leu Val Ser Lys Lys Gly Thr Asp Gly Val Pro
                85                  90                  95

Val Met Leu Gln Thr Asn Phe Phe Arg Leu Lys Thr Lys Pro Glu Trp
                100                 105                 110

Arg Ile Val His Tyr His Val Glu Phe Glu Pro Ser Ile Glu Asn Pro
        115                 120                 125

```
Arg Val Arg Met Gly Val Leu Ser Asn His Ala Asn Leu Leu Gly Ser
    130                 135                 140

Gly Tyr Leu Phe Asp Gly Leu Gln Leu Phe Thr Thr Arg Lys Phe Glu
145                 150                 155                 160

Gln Glu Ile Thr Val Leu Ser Gly Lys Ser Lys Leu Asp Ile Glu Tyr
                165                 170                 175

Lys Ile Ser Ile Lys Phe Val Gly Phe Ile Ser Cys Ala Glu Pro Arg
            180                 185                 190

Phe Leu Gln Val Leu Asn Leu Ile Leu Arg Arg Ser Met Lys Gly Leu
        195                 200                 205

Asn Leu Glu Leu Val Gly Arg Asn Leu Phe Asp Pro Arg Ala Lys Ile
210                 215                 220

Glu Ile Arg Glu Phe Lys Met Glu Leu Trp Pro Gly Tyr Glu Thr Ser
225                 230                 235                 240

Ile Arg Gln His Glu Lys Asp Ile Leu Leu Gly Thr Glu Ile Thr His
                245                 250                 255

Lys Val Met Arg Thr Glu Thr Ile Tyr Asp Ile Met Arg Arg Cys Ser
            260                 265                 270

His Asn Pro Ala Arg His Gln Asp Glu Val Arg Val Asn Val Leu Asp
        275                 280                 285

Leu Ile Val Leu Thr Asp Tyr Asn Asn Arg Thr Tyr Arg Ile Asn Asp
290                 295                 300

Val Asp Phe Gly Gln Thr Pro Lys Ser Thr Phe Ser Cys Lys Gly Arg
305                 310                 315                 320

Asp Ile Ser Phe Val Glu Tyr Tyr Leu Thr Lys Tyr Asn Ile Arg Ile
                325                 330                 335

Arg Asp His Asn Gln Pro Leu Leu Ile Ser Lys Asn Arg Asp Lys Ala
            340                 345                 350

Leu Lys Thr Asn Ala Ser Glu Leu Val Val Leu Ile Pro Glu Leu Cys
        355                 360                 365

Arg Val Thr Gly Leu Asn Ala Glu Met Arg Ser Asn Phe Gln Leu Met
370                 375                 380

Arg Ala Met Ser Ser Tyr Thr Arg Met Asn Pro Lys Gln Arg Thr Asp
385                 390                 395                 400

Arg Leu Arg Ala Phe Asn His Arg Leu Gln Asn Thr Pro Glu Ser Val
                405                 410                 415

Lys Val Leu Arg Asp Trp Asn Met Glu Leu Asp Lys Asn Val Thr Glu
            420                 425                 430

Val Gln Gly Arg Ile Ile Gly Gln Gln Asn Ile Val Phe His Asn Gly
        435                 440                 445

Lys Val Pro Ala Gly Glu Asn Ala Asp Trp Gln Arg His Phe Arg Asp
450                 455                 460

Gln Arg Met Leu Thr Thr Pro Ser Asp Gly Leu Asp Arg Trp Ala Val
465                 470                 475                 480

Ile Ala Pro Gln Arg Asn Ser His Glu Leu Arg Thr Leu Leu Asp Ser
                485                 490                 495

Leu Tyr Arg Ala Ala Ser Gly Met Gly Leu Arg Ile Arg Ser Pro Gln
            500                 505                 510

Glu Phe Ile Ile Tyr Asp Asp Arg Thr Gly Thr Tyr Val Arg Ala Met
        515                 520                 525

Asp Asp Cys Val Arg Ser Asp Pro Lys Leu Ile Leu Cys Leu Val Pro
530                 535                 540

Asn Asp Asn Ala Glu Arg Tyr Ser Ser Ile Lys Lys Arg Gly Tyr Val
```

```
                545                 550                 555                 560
          Asp Arg Ala Val Pro Thr Gln Val Val Thr Leu Lys Thr Lys Lys
                          565                 570                 575
          Pro Tyr Ser Leu Met Ser Ile Ala Thr Lys Ile Ala Ile Gln Leu Asn
                      580                 585                 590
          Cys Lys Leu Gly Tyr Thr Pro Trp Met Ile Glu Leu Pro Leu Ser Gly
                          595                 600                 605
          Leu Met Thr Ile Gly Phe Asp Ile Ala Lys Ser Thr Arg Asp Arg Lys
                      610                 615                 620
          Arg Ala Tyr Gly Ala Leu Ile Ala Ser Met Asp Leu Gln Gln Asn Ser
          625                 630                 635                 640
          Thr Tyr Phe Ser Thr Val Thr Glu Cys Ser Ala Phe Asp Val Leu Ala
                          645                 650                 655
          Asn Thr Leu Trp Pro Met Ile Ala Lys Ala Leu Arg Gln Tyr Gln His
                      660                 665                 670
          Glu His Arg Lys Leu Pro Ser Arg Ile Val Phe Tyr Arg Asp Gly Val
                          675                 680                 685
          Ser Ser Gly Ser Leu Lys Gln Leu Phe Glu Phe Glu Val Lys Asp Ile
          690                 695                 700
          Ile Glu Lys Leu Lys Thr Glu Tyr Ala Arg Val Gln Leu Ser Pro Pro
          705                 710                 715                 720
          Gln Leu Ala Tyr Ile Val Val Thr Arg Ser Met Asn Thr Arg Phe Phe
                          725                 730                 735
          Leu Asn Gly Gln Asn Pro Pro Gly Thr Ile Val Asp Asp Val Ile
                      740                 745                 750
          Thr Leu Pro Glu Arg Tyr Asp Phe Tyr Leu Val Ser Gln Gln Val Arg
                          755                 760                 765
          Gln Gly Thr Val Ser Pro Thr Ser Tyr Asn Val Leu Tyr Ser Ser Met
          770                 775                 780
          Gly Leu Ser Pro Glu Lys Met Gln Lys Leu Thr Tyr Lys Met Cys His
          785                 790                 795                 800
          Leu Tyr Tyr Asn Trp Ser Gly Thr Thr Arg Val Pro Ala Val Cys Gln
                          805                 810                 815
          Tyr Ala Lys Lys Leu Ala Thr Leu Val Gly Thr Asn Leu His Ser Ile
                      820                 825                 830
          Pro Gln Asn Ala Leu Glu Lys Lys Phe Tyr Tyr Leu
                      835                 840

<210> SEQ ID NO 14
<211> LENGTH: 29
<212> TYPE: DNA
<213> ORGANISM: Artificial Sequence
<220> FEATURE:
<223> OTHER INFORMATION: CD34 hematopoietic cell cDNA forward primer

<400> SEQUENCE: 14
atgatctttg gtgtgaacac aaggcagaa                                    29

<210> SEQ ID NO 15
<211> LENGTH: 31
<212> TYPE: DNA
<213> ORGANISM: Artificial Sequence
<220> FEATURE:
<223> OTHER INFORMATION: CD34 hematopoietic cell cDNA reverse primer

<400> SEQUENCE: 15
gaggtagtaa aggcggtttg acagtgacag a                                 31
```

```
<210> SEQ ID NO 16
<211> LENGTH: 24
<212> TYPE: DNA
<213> ORGANISM: Artificial Sequence
<220> FEATURE:
<223> OTHER INFORMATION: human hiwi gene forward primer

<400> SEQUENCE: 16
ccttgccagt acgcccacaa gctg                                              24

<210> SEQ ID NO 17
<211> LENGTH: 27
<212> TYPE: DNA
<213> ORGANISM: Artificial Sequence
<220> FEATURE:
<223> OTHER INFORMATION: human hiwi gene reverse primer

<400> SEQUENCE: 17
ccccacctat ggttgtagtg agcatcc                                           27
```

HUMAN HEMATOPOIETIC GROWTH REGULATORY GENE AND USES

This invention was made with government support under National Institute of Health grant No. HRAF:HL-98-022. The government has certain rights to this invention.

BACKGROUND OF THE INVENTION

1. Field of the Invention

This invention relates to a human hematopoietic growth regulatory gene termed hiwi and genes corresponding thereto. Specifically, the invention relates to the isolation, cloning and sequencing of complementary DNA (cDNA) copies of messenger RNA (mRNA) encoding a novel human hiwi gene. The invention also relates to the construction of recombinant expression constructs comprising cDNA of the novel human hiwi gene, said recombinant expression constructs being capable of expressing hiwi gene product in cultures of transformed prokaryotic and eukaryotic cells. Production of the hiwi gene product in such cultures is also provided. The invention relates to the use of such cultures of such transformed cells to produce homogeneous compositions of the human hiwi gene product. The invention also provides cultures of such cells producing the hiwi protein for the characterization of novel and useful drugs. Antibodies against and epitopes of this novel human hiwi gene product are also provided by the invention. Methods for isolating human hematopoietic stem cells from biological samples such as bone marrow are also provided.

2. Background of the Invention

Stem cells can undergo self-renewal as well as generate differentiated progeny. Hematopoietic stem cells (HSC) have the ability to undergo self-renewal and to differentiate into cells belonging to multiple hematopoietic lineages (Morrison et al., 1995, *Annu Rev Cell Dev Biol*. 11:35–71; Chen et al., 1997, *Immunol Rev*. 157:41–51). The capacity of a hematopoietic stem cell to remain undifferentiated and be capable of reconstituting a myeloablated host as well as its ability to generate multiple differentiated cell types is central to its pivotal role in normal hematopoiesis. These properties allow stem cells to maintain hematopoiesis throughout the lifespan of an organism.

The knowledge of the behavior of HSCs is limited due to their rarity, difficulty of efficient isolation, and their sensitivity to manipulation (Morrison et al., ibid.; Chen et al., ibid.). Despite an improved ability of various laboratories to isolate and manipulate pure populations of murine and human HSCs (Goodell, 1999, *Blood* 94:2545–2547; Huang et al., 1999, *Blood* 94:2595–2604) current understanding of mechanisms by which a stem cell divides and retains its unique biological properties has eluded the efforts of a large number of investigators (Vaziri et al., 1994, *Proc Natl Acad Sci. USA* 91:9857–9860; Lansdorp et al., 1995, *Exp Hematol*. 23:187–191; van der Loo et al., 1995, *Blood* 85:2598–2606; Peters et al., 1995, *Exp Hematol*. 23:461–469; Peters et al., 1996, *Blood* 87:30–37; Yonemura et al., 1996, *Proc Natl Acad Sci. USA* 93:4040–4044).

Elucidation of the genetic program that underlies the unique biological properties of HSCs has been the focus of a growing number of laboratory groups (Vaziri et al., ibid.; Lansdorp et al., ibid.) using a variety of approaches. Array technology, for instance, now permits simultaneous monitoring of expression patterns of thousands of genes during cellular differentiation and response (van der Loo et al., ibid.; Peters et al., ibid.). The key to the successful implementation of such technology to the study of stem cell biology is the development of the means to assign priority to such genes and to determine their function.

The self-renewal capacity of several classes of stem cells is thought to be controlled by external signals and intrinsic cellular processes (Morrison et al., ibid.; Chen et al., ibid.; Bruno et al., 1995, *Exp Hematol*. 23:1212–1217; Hoffman, 1999, *Curr Opin Hematol*. 6:184–191). Over the last 2 decades, a variety of external stimuli (cytokines, matrix proteins) that alter HSC self-renewal have been the subject of intense investigation. Although a number of such external signals that interact with specific receptors on HSC have been identified, the signaling mechanisms that govern HSC self-renewal have eluded investigation.

A different approach to analyze the genetic organization of human HSCs is to analyze expression of genes originally shown to affect stem cell development in lower species (Peters et al., ibid.; Yonemura et al., ibid.; Zon 1995, *Blood* 86:2876–2891). In these experiments, genes that were originally shown to affect stem cell development in lower species have been shown subsequently to be expressed by human hematopoietic cells and to have profound regulatory effect on human hematopoiesis. Lower organisms such as Drosophilae, *C. elegans* and *D. rerio* (zebra fish) have been utilized as effective models for studying mechanisms that are conserved among diverse developmental systems (Lewis, 1978, *Nature* 276:565–570; Zon, 1995, ibid.; Tabara et al., 1999, *Cell* 99:123–132). Studies from *Xenopus*, for instance, have revealed a multitude of genes involved in mesoderm induction including members of the transforming growth factor β superfamily, fibroblast growth factor and at least 19 members of the Wnt gene family have been identified in diverse species ranging from roundworm and insects to humans (Sidow, 1992, *Proc Natl Acad Sci. USA* 89:5098–5102; Austin et al., 1997, *Blood* 89:3624–3635). Wnt gene family members have subsequently been shown to have profound effects on murine and human hematopoiesis.

Intrinsic cellular mechanisms that regulate stem cell self-renewal have been explored in a variety of model systems including germ line stem cells (GSCs) in several lower species. *Drosophila* has been a particularly useful model for studying biological processes that are conserved in higher developmental systems (Lewis, ibid.; Nusslein-Volhard et al., 1980, *Nature* 287:795–801; Lin & Spradling, 1993, *Dev Biol*. 159:140–152; Lin et al., 1997, *Development* 124:2463–2476; Lin, 1998, *Curr Opin Cell Biol*. 10:687–693; Cox et al., 1998, *Genes Dev*. 12:3715–3727; Lin, 1999, *Annu Rev Genet*. 31:455–491; Benfey, 1999, *Curr Biol*. R171). In *Drosophila*, stem cells exist in the germ line at the apical tip of each ovariole, the germarium, which is the functional portion of the ovary (Lin & Spradling, ibid.; King, 1970, OVARIAN DEVELOPMENT IN *DROSOPHILA MELANOGASTER*, New York: McGraw-Hill). Each ovary consists of 10–17 ovarioles. Each germarium contains 2 to 3 GSCs that are in direct contact with specialized somatic cells, the basal terminal filament cells (King, 1970, ibid.; Lin, 1998, ibid; Lin, 1999, ibid.). GSCs undergo asymmetric divisions to produce daughter stem cells and a differentiated daughter cell, a cystoblast. The GSCs provide a continuous source of totipotent cells for the production of gametes needed for fertilization (Lin, 1999, ibid.). They are very similar to HSCs in their ability to not only self-renew but to remain capable of generating large numbers of differentiated daughter cells (Lin, 1999, ibid.; Benfey, 1999, ibid.). The intracellular mechanisms which serve as the determinants of asymmetric-segregating cell fates of GSCs depend not only on the basic cell cycle machinery but also on a family of recently identified genes, some of which are evolutionarily conserved (Cox et al., 1998, ibid.; Benfey, 1999, ibid,). A group of somatic cells in *Drosophila*, termed terminal filament cells, which are distal and immediately adjacent to the GSCs, have been shown to regulate GSC division (Lin, 1998, ibid.; Lin, 1999, ibid.; Lin & Spradling, ibid). Laser ablation of the terminal filament increases the rate of oogenesis by 40% (Lin & Spradling, ibid.).

Recently a number of genes including dpp, piwi, pumilio and fs(1)Yb have been identified and shown to be essential for GSC maintenance (Lin & Spradling, ibid.; Cox et al., 1998, ibid.; King & Lin, 1999, *Development* 126:1833–1844). Among these genes, piwi has been of special interest. It has recently has been demonstrated to be an essential stem cell gene in *Drosophila* and *C. elegans* and to be expressed in tissues belonging to many species including human. The *Drosophila* piwi gene is required for asymmetric division of GSCs but is not required for differentiation of committed daughter cells. piwi expression in adjacent somatic cells, terminal filament cells, regulates GSC division (Cox et al., 1998, ibid.). Loss-of-function mutations in the piwi gene found in the terminal filament leads to a failure of stem cell maintenanc3 (Lin & Spradling, ibid.; Cox et al., 1998, ibid.); piwi is expressed not only in the terminal filament but also in the germ line. Loss of piwi function in the germ line, however, is not known to affect GSC division. The protein encoded by piwi is extraordinarily well conserved along the evolutionary tree, being found in both *Caenorhabditis elegans* and primates (Cox et al., 1998, ibid).

Thus, there is a need in the art to identify genes and gene products in hematopoietic stem cells that regulate cell cycling and proliferation. There further is a need in the art to identify a human homolog for the *Drosophila* piwi gene to determine the role of said homolog in hematopoietic stem cell development and maintenance. There is also a need in the art to develop drugs and other active agents for controlling, promoting or inhibiting hematopoietic stem cell growth, proliferation and differentiation to permit manipulation of hematopoietic stem cells and provide renewable sources of said stem cells. There is additionally a need for developing compounds to inhibit leukemia cell growth and induce apoptosis of such cells as a means of cancer treatment.

SUMMARY OF THE INVENTION

The present invention relates to the cloning, expression and functional characterization of a human hematopoietic growth regulatory gene termed hiwi. The invention comprises nucleic acids having a nucleotide sequence of a novel human hiwi gene. The nucleic acids provided by the invention comprise a complementary DNA (cDNA) copy of the corresponding mRNA transcribed in vivo from the human hiwi gene of the invention. In one preferred embodiment, the human hiwi gene encodes a protein having an amino acid sequence identified by SEQ ID NO. 2. In another preferred embodiment, the human hiwi gene has a nucleic acid sequence identified by SEQ ID NO. 1. Also provided are the deduced amino acid sequence of the cognate proteins of the cDNAs provided by the invention, methods of making said cognate proteins by expressing the cDNAs in cells transformed with recombinant expression constructs comprising said cDNAs, and said recombinant expression constructs and cells transformed thereby.

This invention in a first aspect provides nucleic acids, nucleic acid hybridization probes, recombinant eukaryotic expression constructs capable of expressing the human hiwi gene of the invention in cultures of transformed cells, and such cultures of transformed eukaryotic cells that synthesize the human hiwi gene. In another aspect, the invention provides homogeneous compositions of the human hiwi gene product of the invention, and membrane and cytosolic preparations from cells expressing the human hiwi gene product, as well as antibodies against and epitopes of the human hiwi gene product. The invention in another aspect provides methods for making said homogenous preparations and membrane and cytosolic preparations using cells transformed with the recombinant expression constructs of the invention and expressing said human hiwi gene product thereby. Methods for characterizing the biochemical properties of the human hiwi gene product and methods for using these proteins in the development of agents having pharmacological uses related to the hiwi gene product are also provided by the invention.

In a first aspect, the invention provides a nucleic acid having a nucleotide sequence encoding a human hiwi gene. In a preferred embodiment, the nucleic acid encodes a nucleotide sequence comprising 2328 basepairs (bp) encoding a 776 amino acid sequence. In this embodiment of the invention, the nucleotide sequence of the human hiwi gene is the nucleotide sequence depicted in FIG. 1 (SEQ ID No: 1). The sequence shown in FIG. 1 will be understood to represent one specific embodiment of a multiplicity of nucleotide sequences that encode the human hiwi gene amino acid sequence (SEQ ID No.: 2) of the invention and that these different nucleotide sequences are functionally equivalent and are intended to be encompassed by the claimed invention. In addition, it will be understood that different organisms and cells derived therefrom express preferentially certain tRNAs corresponding to subsets of the degenerate collection of tRNAs capable of encoding certain of the naturally-occurring amino acids, and that embodiments of the multiplicity of nucleotide sequences encoding the amino acid sequence of the human hiwi gene product of the invention that are optimized for expression in specific prokaryotic and eukaryotic cells are also encompassed by the claimed invention. Isolated nucleic acid derived from human genomic DNA and isolated by conventional methods using the human cDNA provided by the invention is also within the scope of the claimed invention. Finally, it will be understood that allelic variations of the human hiwi gene, including naturally occurring and in vitro modifications thereof are within the scope of this invention. Each such variant will be understood to have essentially the same amino acid sequence as the sequence of the human hiwi gene product disclosed herein.

The human hiwi gene product corresponding to the human cDNA of the invention is a second aspect of the claimed invention. In a preferred embodiment, the human hiwi gene is encoded by a nucleic acid having a deduced amino acid sequence shown in FIG. 1 (SEQ ID No.: 2). Also provided are preparations of said human hiwi gene product comprising a membrane or cytosolic preparation from a cell, most preferably a recombinant cell, expressing a nucleic acid encoding a human hiwi gene.

As provided in this aspect of the invention is a homogeneous composition of a human hiwi gene product having a molecular weight of about 90 kD or derivative thereof and having an amino acid sequence shown in FIG. 1 and identified by SEQ ID No.: 2, said size being understood to be the predicted size of the protein before any post-translational modifications thereof.

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clone of the invention encoding a human hiwi gene or fragment thereof, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of the human hiwi gene in various tissues of mammals, including humans. It is also an object of the present invention to provide nucleic acid hybridization probes derived from the sequences of human hiwi gene of the invention to be used for the detection and diagnosis of diseases and pathological conditions associated with differential expression of the human hiwi gene. It is an object of this invention to provide nucleic acid hybridization probes derived from the nucleic acid sequences of the human hiwi gene herein disclosed to be used for the detection of novel related genes.

The present invention also includes synthetic peptides made using the nucleotide sequence information comprising the cDNA embodiments of the invention. The invention includes either naturally occurring or synthetic peptides which may be used as antigens for the production of human hiwi gene product-specific antibodies, or useful as competitors of human hiwi gene product molecules for agonist, antagonist or drug binding, or to be used for the production of inhibitors of binding with agonists, antagonists, analogues thereof or any other binding partner.

The present invention also provides antibodies against and epitopes of the human hiwi gene product molecules of the invention. It is an object of the present invention to provide antibodies that are immunologically reactive to the human hiwi gene product. It is a particular object to provide monoclonal antibodies against the human hiwi gene product. Hybridoma cell lines producing such antibodies are also objects of the invention. It is envisioned that such hybridoma cell lines may be produced as the result of fusion between a non-immunoglobulin producing mouse myeloma cell line and spleen cells derived from a mouse immunized with a cell line which expresses antigens or epitopes of a human hiwi gene product of the invention. The present invention also provides hybridoma cell lines that produce such antibodies, and can be injected into a living mouse to provide an ascites fluid from the mouse that is comprised of such antibodies. It is a further object of the invention to provide immunologically-active epitopes of the human hiwi gene product. Chimeric antibodies immunologically reactive against the human hiwi gene product are also within the scope of this invention.

The present invention provides recombinant expression constructs comprising a nucleic acid encoding a human hiwi gene of the invention wherein the construct is capable of expressing the encoded human hiwi gene product in cultures of cells transformed with the construct. A preferred embodiment of such constructs comprises a human hiwi gene cDNA depicted in FIG. 1 (SEQ ID No.: 1), such constructs being capable of expressing the human hiwi gene product encoded therein in cells transformed with the construct.

The invention also provides prokaryotic and more preferably eukaryotic cells transformed with the recombinant expression constructs of the invention, each such cells being capable of and indeed expressing the human hiwi gene product encoded in the transforming construct, as well as methods for preparing human hiwi gene-encoded protein using said transformed cells.

The present invention also includes within its scope protein preparations of prokaryotic and eukaryotic cell membranes comprising the human hiwi gene-encoded protein of the invention, derived from cultures of prokaryotic or eukaryotic cells, respectively, transformed with the recombinant expression constructs of the invention. The present invention also includes within its scope protein preparations of prokaryotic and eukaryotic cytoplasmic fractions containing the human hiwi gene-encoded protein of the invention, derived from cultures of prokaryotic or eukaryotic cells, respectively, transformed with the recombinant expression constructs of the invention.

The invention also provides methods identifying a compound that induces or increases hiwi gene expression in mammalian cells, preferably a human cell, most preferably a leukemia cell or a hematopoietic stem cell. In these embodiments, the method comprises the steps of culturing a mammalian cell under conditions wherein the cell does not express the hiwi gene or expresses an amount of the hiwi gene product insufficient to repress cell proliferation; contacting the cell with a test compound for a time period; assaying the cells at intervals during the time period for hiwi gene expression and cell proliferation or apoptosis; and identifying compounds that induce hiwi gene expression, and concomitantly decrease cell proliferation or increase the percentage of cells undergoing apoptosis or both. Compounds that induce or increase hiwi gene expression in mammalian cells, preferably a human cell, most preferably a leukemia cell or a hematopoietic stem cell are also provided by the invention.

The invention also provides methods for maintaining or increasing the percentage of hematopoietic stem cells, preferably human hematopoietic stem cells, and most preferably $CD34^+$ human hematopoietic stem cells, from biological samples comprising said stem cells, most preferably bone marrow samples or peripheral blood samples. The method comprises the step of increasing hiwi gene product expression in said cells. In preferred embodiments, the method comprises the step of culturing the cells in the presence of a hiwi gene-inducing compound identified by the methods of the invention. In alternative preferred embodiment, the method comprises the step of introducing into said cells a recombinant expression construct of the invention encoding a hiwi gene, most preferably a human hiwi gene. In preferred embodiments, the hiwi gene encodes a gene product having an amino acid sequence identified by SEQ ID NO. 2. In preferred embodiments, expression of the hiwi gene is inducible gene expression.

Specific preferred embodiments of the present invention will become evident from the following more detailed description of certain preferred embodiments and the claims.

DESCRIPTION OF THE DRAWINGS

FIG. 1 illustrates the nucleotide (SEQ ID No.: 1) and amino acid (SEQ ID No.: 2) sequences of a human hiwi gene product and *Drosophila* piwi protein.

Figure 2:
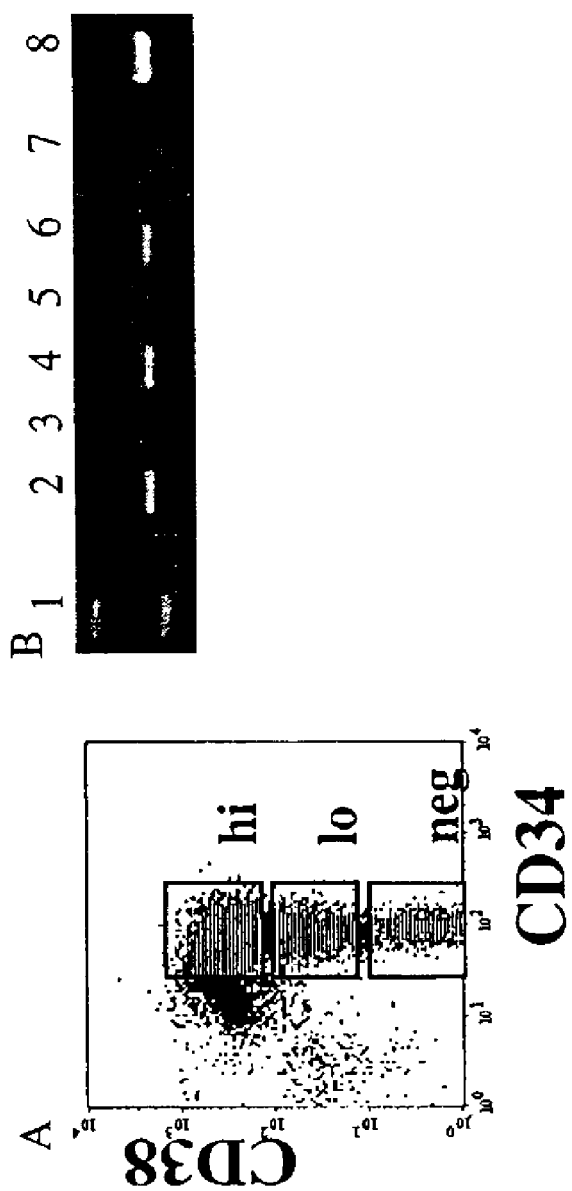
FIG. 2A is a fluorescence-activated cell sorting (FACS) analysis of CD34 and CD38 (hi, lo and negative) expressing human adult bone marrow cells.
FIG. 2B is a photograph of an ethidium bromide stained gel electrophoretic analysis of DNA fragments produced by reverse transcriptase-polymerase chain reaction (RT-PCR)

analysis of RNA isolated from CD34 and CD38 expressing human adult bone marrow cells. Lane 1 is a 123 bp size marker; lane 2 is the fragment produced from CD34$^+$CD38$^-$ cells; lane 3 is the fragment produced from CD34$^+$CD38$^-$ cells without reverse transcription of cellular RNA; lane 4 is the fragment produced from CD34$^+$CD38$^{lo}$ cells; lane 5 is the fragment produced from CD34$^+$CD38$^{lo}$ cells without reverse transcription of cellular RNA; lane 6 is the fragment produced from CD34$^+$CD38$^{hi}$ cells; lane 7 is the fragment produced from CD34$^+$CD38$^{hi}$ cells without reverse transcription of cellular RNA; lane 8 is a negative control (water); lane 9 is a positive control (human testis).

FIGS. 3A through 3C is a photograph of an ethidium bromide stained gel electrophoretic analysis of DNA fragments produced by RT-PCR analysis of RNA isolated from human leukemia cell lines. In FIG. 3A, lane 1 is a 1 kilobase size marker; lane 2 is the fragment produced from TF1 cells; lane 3 is the fragment produced from Jurkat cells; lane 4 is the fragment produced from KG1a cells; lane 5 is the fragment produced from KG1 cells; lane 6 is the fragment produced from K562 cells; lane 7 is the fragment produced from CEM cells; lane 8 is the fragment produced from BV173 cells; lane 9 is the fragment produced from SUPB13cells; lane 10 is a negative control (water); lane 11 is a positive control (human testis). FIG. 3B is PCR analysis of the samples in lanes 2–6 of FIG. 3A performed without reverse transcription of cellular RNA. FIG. 3C is RT-PCR analysis of a GAPD internal control.

Figure 4:
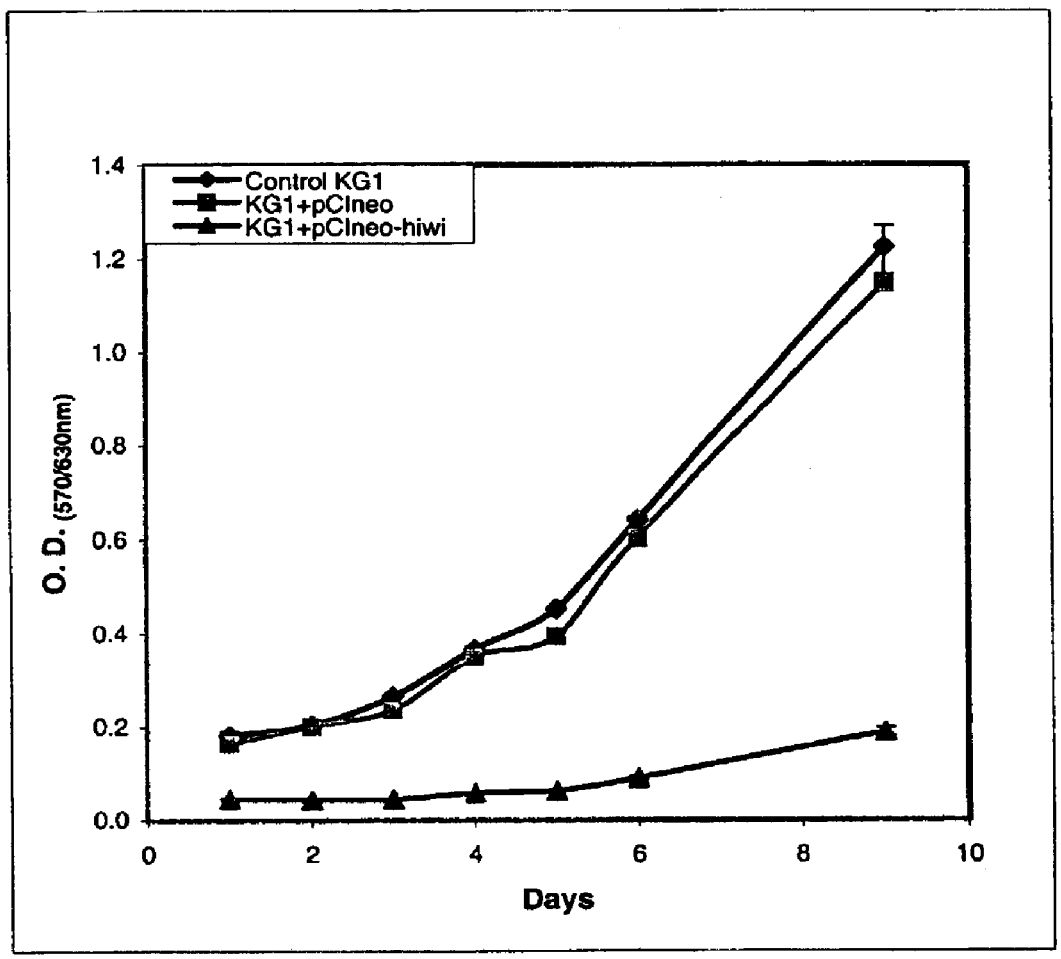

FIG. 4 is a graph of MTT exclusion analysis of control KG1 cells, KG 1 cells transfected with pCIneo vector and KG1 cells transfected with pCIneo-hiwi.

FIGS. 5A through 5C is a photograph of an ethidium bromide stained gel electrophoretic analysis of DNA fragments produced by RT-PCR analysis of RNA isolated from human leukemia cell lines. In FIG. 5A, lane 1 is a 1 kilobase size marker; lanes 2–8 are mock-transfected KG1 cells from days 1–6 and day 9, respectively; lanes 9–15 are vector-transfected KG1 cells from days 1–6 and day 9, respectively; and lanes 16–21 are hiwi-containing vector-transfected KG1 cells from days 1–6 and day 9, respectively. FIG. 5B is PCR analysis of the samples in FIG. 5A performed without reverse transcription of cellular RNA. FIG. 5C is RT-PCR analysis of a GAPD internal control.

Figure 6:
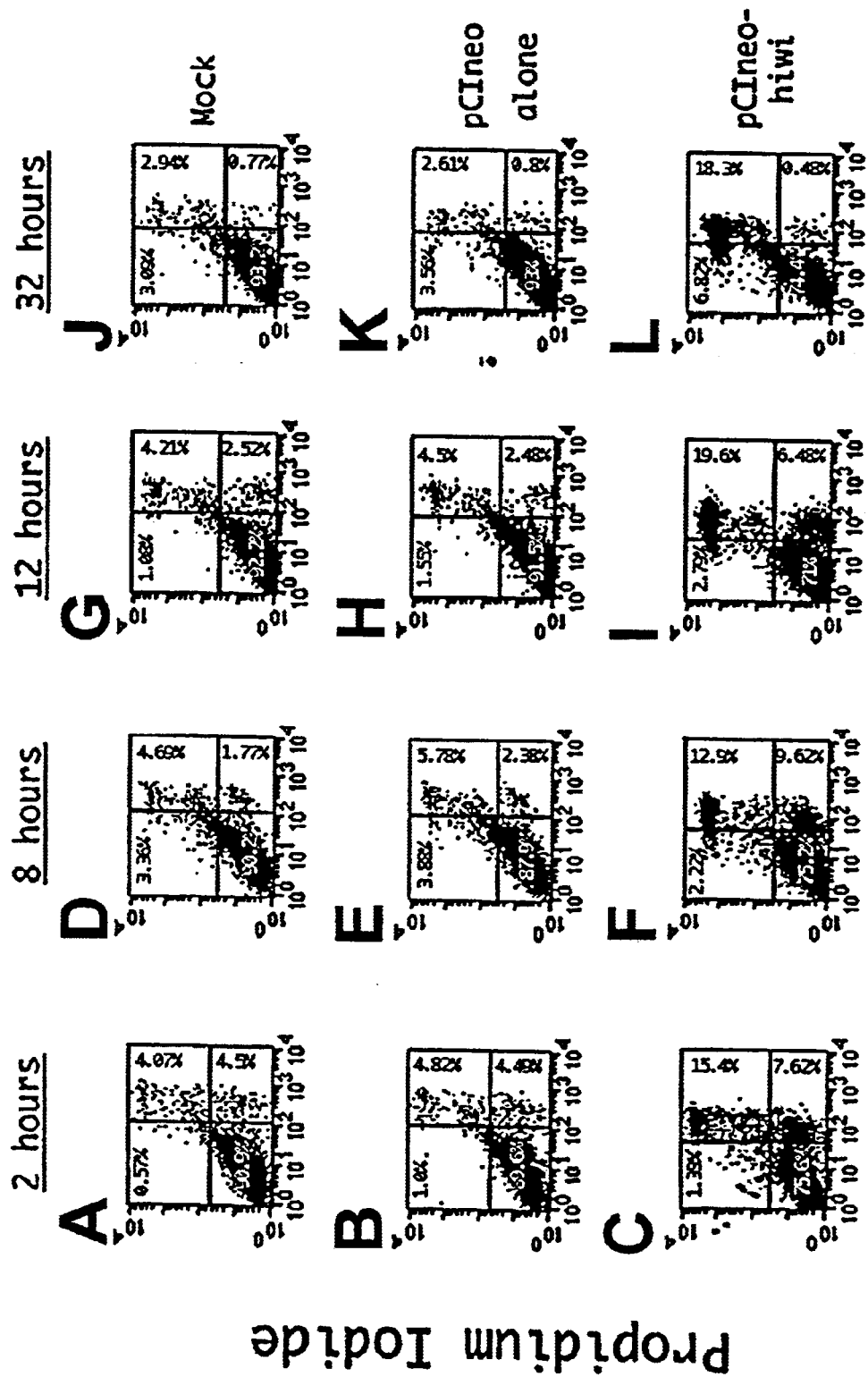

FIGS. 6A through 6L are FACS analyses of apoptosis in KG1 cells (FIGS. 6A, 6D, 6G and 6J), pCIneo vector-transfected KG1 cells (FIGS. 6B, 6E, 6H and 6K) and hiwi-containing pCIneo vector-transfected KG1 cells (FIGS. 6C, 6F, 6I and 6L). FIGS. 6A–C are from cells incubated for 2 hours; FIGS. 6D–F are from cells incubated for 8 hours; FIGS. 6G–I are for cells incubated for 12 hours; and FIGS. 6J–L are for cells incubated for 32 hours.

Figure 7:
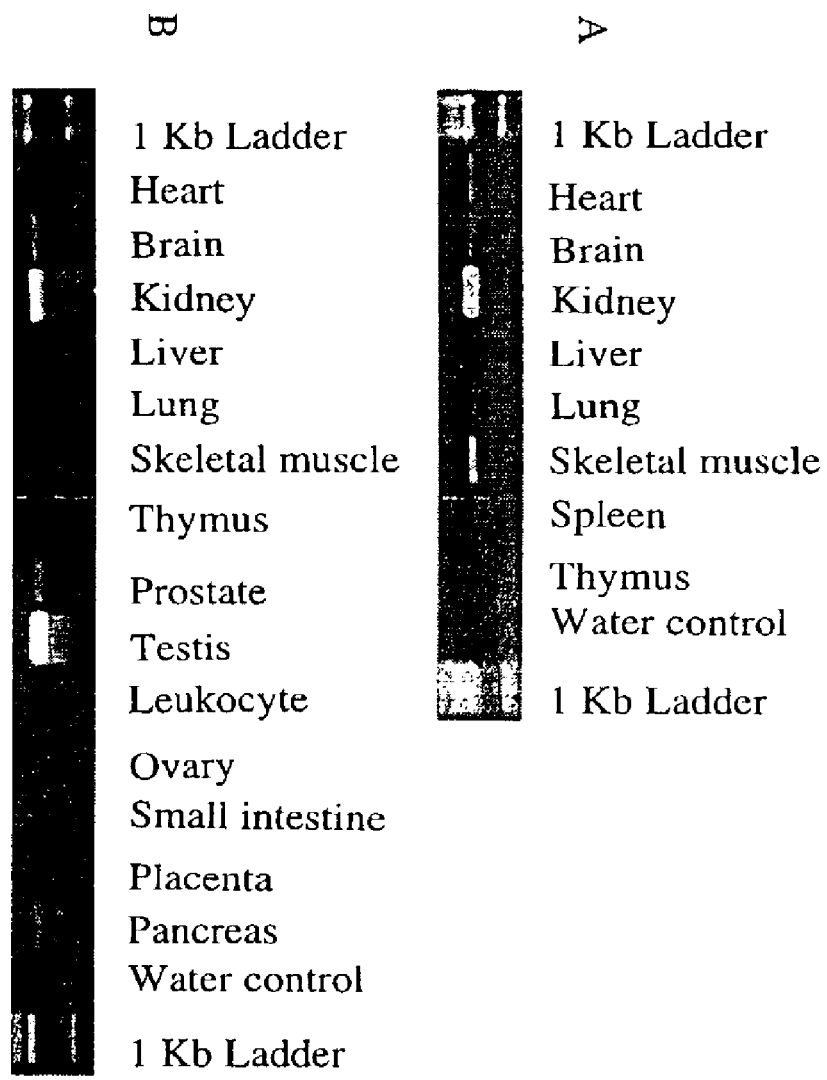

FIGS. 7A and 7B are photographs of ethidium bromide stained gel electrophoretic analyses of DNA fragments produced by RT-PCR analysis of RNA isolated from human fetal tissues (FIG. 7A) and human adult tissues (FIG. 7B) for hiwi RNA.

Figure 8:
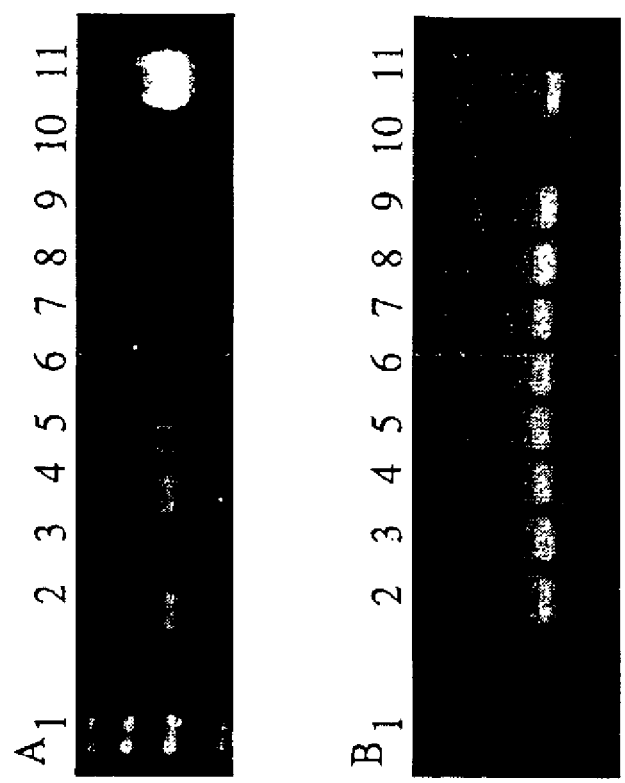

FIGS. 8A and 8B are photographs of ethidium bromide stained gel electrophoretic analyses of DNA fragments produced by RT-PCR analysis of RNA isolated from human CD34$^+$ bone marrow cells. In FIG. 8A, lane 1 is a 123 bp size marker; lane 2 is the fragment produced on day 0 from CD34$^+$ cells; lane 3 is the fragment produced on day 0 from CD34$^-$ cells; lane 4 is the fragment produced from day 1 culture sample; lane 5 is the fragment produced from day 3 culture sample; lane 6 is the fragment produced from day 5 culture sample; lane 7 is the fragment produced from day 7 culture sample; lane 8 is the fragment produced from day 10 culture sample; lane 9 is the fragment produced from day 14 culture sample; lane 10 is a negative control (water); lane 11 is a positive control (human testis). FIG. 8B is RT-PCR analysis of a $\beta_2$ microglobulin internal control.

Figure 9:

FIG. 9 is a photograph of a human metaphase chromosome preparation hybridized with a fluorescence-labeled human hiwi gene probe.

Figure 10:
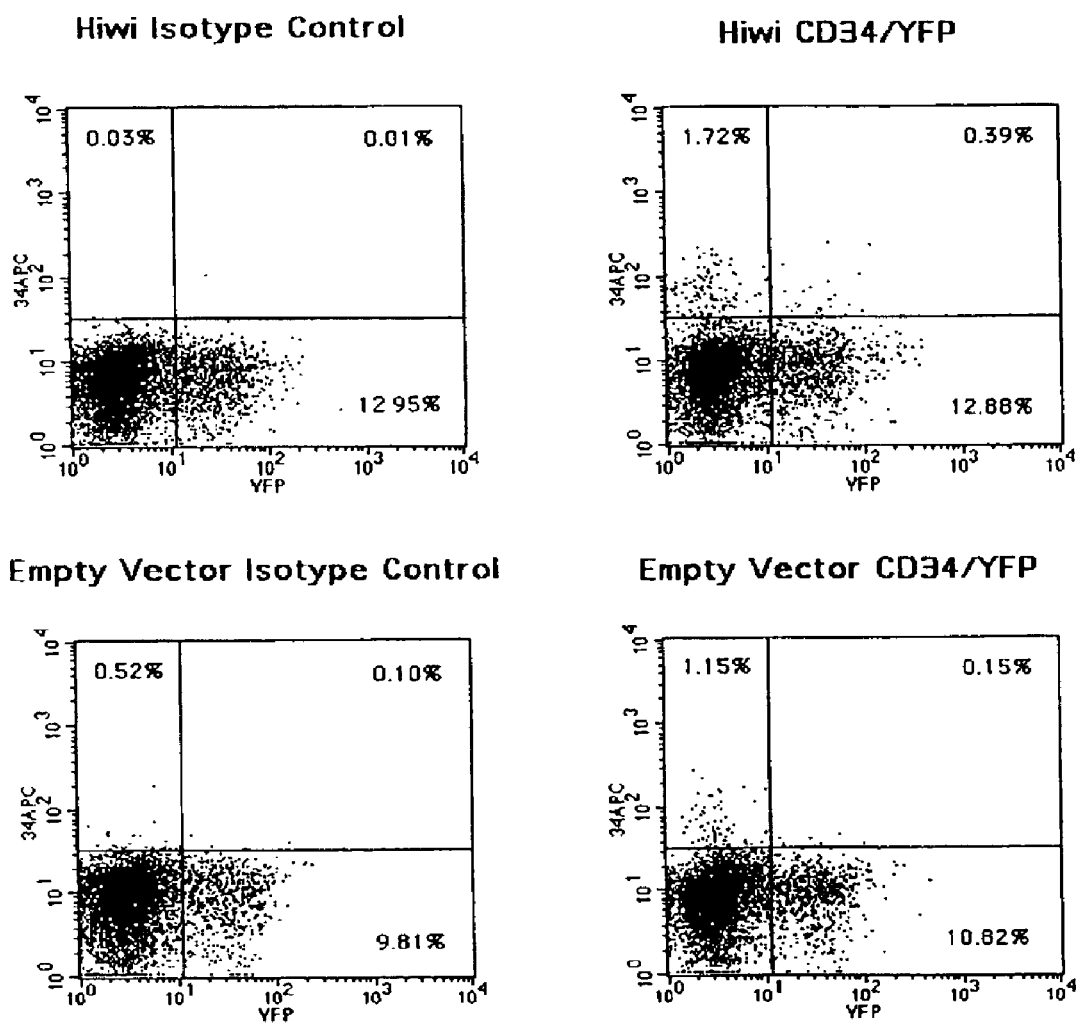

FIG. 10 shows flow cytometric analysis of mock-transfected, vector-transfected and hiwi-containing vector transfected KG1 cells.

DETAILED DESCRIPTION OF THE PREFERRED EMBODIMENTS

The terms "human hiwi gene product" and "human hiwi gene-encoded protein" as used herein refer to proteins consisting essentially of, and having substantially the same biological activity as, the protein encoded by the amino acid depicted in FIG. 1 (SEQ ID No.: 2). This definition is intended to encompass natural allelic variations in the disclosed human hiwi gene product. Cloned nucleic acid provided by the present invention may encode hiwi gene product of any mammalian species of origin, but preferably the nucleic acid provided by the invention encodes hiwi gene product of human origin.

The nucleic acids provided by the invention comprise DNA or RNA having a nucleotide sequence encoding a human hiwi gene product. Specific embodiments of said nucleic acid is depicted in FIG. 1 (SEQ ID No.: 1), and include any nucleotide sequence encoding a hiwi gene product having an amino acid sequence as depicted in FIG. 1 (SEQ ID No.: 2). Nucleic hybridization probes as provided by the invention comprise any portion of a nucleic acid of the invention effective in nucleic acid hybridization under stringency conditions sufficient for specific hybridization. Mixtures of such nucleic acid hybridization probes are also within the scope of this embodiment of the invention. Nucleic acid probes as provided herein are useful for isolating mammalian species analogues of the specific embodiments of the nucleic acids provided by the invention. Nucleic acid probes as provided herein are also useful for detecting human hiwi gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are also useful for Southern hybridization of mammalian, preferably human, genomic DNA for screening for restriction fragment length polymorphism (RFLP) associated with certain genetic disorders and diseases related to differential human hiwi gene expression.

The production of proteins such as human hiwi gene product from cloned genes by genetic engineering means is well known in this art. The discussion that follows is accordingly intended as an overview of this field, and is not intended to reflect the full state of the art.

Nucleic acid encoding a human hiwi gene product may be obtained, in view of the instant disclosure, by chemical synthesis, by screening reverse transcripts of mRNA from appropriate cells or cell line cultures, by screening genomic libraries from appropriate cells, or by combinations of these procedures, in accordance with known procedures as illustrated below. Additionally, sequences of a human hiwi gene product can be obtained from human genomic DNA that has been determined and assembled in a database or other searchable compilation, using search programs known in the art and the sequences of the human hiwi gene product disclosed herein. Screening of mRNA or genomic DNA may be carried out with oligonucleotide probes generated from the nucleic acid sequence information from human hiwi gene encoding nucleic acid as disclosed herein. Probes may be labeled with a detectable group such as a fluorescent group, a radioactive atom or a chemiluminescent group in accordance with known procedures and used in conventional hybridization assays, as described in greater detail in the Examples below. In the alternative, human hiwi gene-encoding nucleic acid sequences may be obtained by use of the polymerase chain reaction (PCR) procedure, using PCR oligonucleotide primers corresponding to nucleic acid sequence information derived from a human hiwi gene as provided herein. See U.S. Pat. Nos. 4,683,195 to Mullis et al. and 4,683,202 to Mullis.

Nucleic acid and oligonucleotide probes as provided by the present invention are useful as diagnostic tools for probing human hiwi gene expression in tissues of humans and other animals. For example, tissues are probed in situ with oligonucleotide probes carrying detectable groups by conventional autoradiographic or other detection techniques, to investigate native expression of the hiwi gene product or pathological conditions relating thereto. Further, chromosomes can be probed to investigate the presence or absence of the corresponding human hiwi gene, and potential pathological conditions related thereto.

Human hiwi gene product may be synthesized in host cells transformed with a recombinant expression construct comprising a nucleic acid encoding said gene and comprising genomic DNA or cDNA. Such recombinant expression constructs can also be comprised of a vector that is a replicable DNA construct. Vectors are used herein either to amplify DNA encoding a human hiwi gene product and/or to express DNA encoding a human hiwi gene. For the purposes of this invention, a recombinant expression construct is a replicable DNA construct in which a nucleic acid encoding a human hiwi gene is operably linked to suitable control sequences capable of effecting the expression of the hiwi gene product in a suitable host.

The need for such control sequences will vary depending upon the host selected and the transformation method chosen. Generally, control sequences include a transcriptional promoter, an optional operator or enhancer sequence to control transcription, a sequence encoding suitable mRNA ribosomal binding sites, and sequences that control the termination of transcription and translation. Amplification vectors do not require expression control domains. All that is needed is the ability to replicate in a host, usually conferred by an origin of replication, and a selection gene to facilitate recognition of transformants. See, Sambrook et al., 2001, *Molecular Cloning: A Laboratory Manual*, 3$^{rd}$ ed. (Cold Spring Harbor Press: New York).

Vectors useful for practicing the present invention include plasmids, viruses (including phage and mammalian DNA and RNA viruses, particularly adenovirus, adeno-associated virus, lentivirus, and retroviruses), and integratable DNA fragments (i.e., fragments integratable into the host genome by homologous recombination). The vector can replicate the gene of interest and function independently of the host genome, or can, in some instances, integrate into the genome itself. Suitable vectors will contain replicon and control sequences which are derived from species compatible with the intended expression host. A preferred vector is pCIneo (obtained from Promega, Madison, Wis.). In preferred embodiments, the recombinant expression construct is an inducible construct wherein expression of the hiwi gene product can be induced in the cell by an effector molecule. The term "inducible" is intended to encompass vectors wherein expression of the hiwi gene product is activated, in either transcription or translation by an effector molecule, most preferably a small molecule or metabolite, wherein induction of hiwi gene expression is achieved by contacting the cell with the effector molecule. Examples of effector molecules and inducible expression include but are not limited to glucocorticoids and recombinant expression constructs having hiwi gene expression mediated by a glucocorticoid-responsive promoter; heavy metal ions such as cadmium and recombinant expression constructs having hiwi gene expression mediated by a metallothionine promoter; and isopropylthiogalactoside (IPTG) and recombinant expression constructs having hiwi gene expression mediated by a promoter comprising all or a functional portion of the bacterial lac operon, and further encoding a constitutively expressing a lac repressor protein or mammalian or genetically-engineered homolog thereof. See Labow et al., 1990, *Molec. Cell. Biol.* 10: 3343–3356.

The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, *Bioscience Reports* 7: 107–112; Smithies et al., 1985, Nature 317: –234.

Transformed host cells are cells that have been transformed or transfected with recombinant expression constructs made using recombinant DNA techniques and comprising nucleic acid encoding a human hiwi gene product. Cultures of cells derived from multicellular organisms are a desirable host for recombinant human hiwi gene product synthesis. In principal, any higher eukaryotic cell culture is useful, whether from vertebrate or invertebrate culture. However, mammalian cells are preferred, as illustrated in the Examples, and particularly mammalian cells, most preferably human cells, that do not express an endogenous hiwi gene. Propagation of such cells in cell culture has become a routine procedure. See *Tissue Culture*, Academic Press, Kruse & Patterson, editors (1973). Examples of useful host cell lines are human KG1 leukemia cells, human embryonic kidney (HEK) 293 cells, HeLa cells, Chinese hamster ovary (CHO) cell lines, mouse Ltk$^-$ cell lines, COS-7, CV1, BHK, and MDCK cell lines. Preferred host cells are HEK293 cells, COS-7 cells (Gluzman, 1981, *Cell* 23: 175–182) and Ltk$^-$ cells. Transformed host cells may express the human hiwi gene product, but host cells transformed for purposes of cloning or amplifying nucleic acid hybridization probe DNA need not express the human hiwi gene. The human hiwi gene product of the invention can be located in the host cell cytosol. Accordingly, the invention provides preparations of cell cytosolic fractions comprising the human hiwi gene product of the invention, as well as purified, homogeneous preparations of the human hiwi gene product itself. See, Sambrook et al., ibid. The human hiwi gene product of the invention can be located in the host cell nucleus. Accordingly, the invention provides preparations of cell nuclear fractions comprising the human hiwi gene product of the invention, as well as purified, homogeneous preparations of the human hiwi gene product itself. The human hiwi gene product of the invention may also be located in or associated with membranes from the host cell. Therefore, the invention provides preparations of said cell membranes comprising the human hiwi gene product of the invention. See, Sambrook et al., ibid.

The invention provides homogeneous compositions of human hiwi gene product produced by transformed eukaryotic cells as provided herein. Each such homogeneous composition is intended to be comprised of a human hiwi gene product that comprises at least 75%, more preferably at least 80%, and most preferably at least 90% of the protein in such a homogenous composition; in said homogeneous preparations, individual contaminating protein species are expected to comprise less than 5%, more preferably less than 2% and most preferably less than 1% of the preparation. The invention also provides membrane and cytosolic preparations from cells expressing human hiwi gene product as the result of transformation with a recombinant expression construct, as described herein.

Human hiwi gene product preparations as provided herewith are useful for identifying compounds that interfere with expression of the hiwi gene or activity of the hiwi gene product. A compound identified in a screen may be useful for treating various conditions associated with effects of unregulated human hiwi gene product activity as a result of endogenous or exogenous over- or underexpression. The present invention provides a pharmaceutical composition comprising the compound in admixture with a pharmaceutically acceptable carrier. In a preferred embodiment, a therapeutically effective amount of the pharmaceutical composition is administered to a patient with a condition associated with unregulated human hiwi gene product.

The invention also provides methods for identifying compounds that induce or increase hiwi gene expression in mammalian cells, preferably leukemia cells or hematopoietic stem cells and most preferably human leukemia cells and human hematopoietic stem cells, especially $CD34^+$ human hematopoietic stem cells. In these embodiments, the method comprises the steps of culturing a mammalian, most preferably a human cell, most preferably a leukemia cell or hematopoietic stem cell under conditions wherein the cell does not express the hiwi gene or expresses an amount of the hiwi gene product insufficient to repress cell proliferation. The method further comprises the steps of contacting the cell with a test compound for a time period, and assaying the cells at intervals during the time period for hiwi gene expression and cell proliferation or apoptosis. Compounds that induce hiwi gene expression, and concomitantly decrease cell proliferation or increase the percentage of cells undergoing apoptosis are identified thereby.

The method also provides compounds identified by these methods. In preferred embodiments, the compounds induce both hiwi gene expression and quiescence in human hematopoietic stems cells, or induce hiwi expression and inhibit proliferation or promote apoptosis or both in human leukemia cells. Pharmaceutical compositions prepared from such compounds identified by the methods of the invention are also beneficially provided.

Pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes. Pharmaceutical compositions of the compounds of the present invention can be formulated and administered through a variety of means, including systemic, localized, or topical administration. Techniques for formulation and administration can be found in "Remington's Pharmaceutical Sciences," Mack Publishing Co., Easton, Pa. Pharmaceutical compositions for use in accordance with the present invention thus can be formulated in conventional manner using one or more physiologically acceptable carriers comprising excipients and auxilaries that facilitate processing of the active compounds into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0–4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

For injection, the compounds of the invention can be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active compounds in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the active compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the active compound and a suitable powder base such as lactose or starch.

The active compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active compounds can be in powder form for constitution with a suitable vehicle, e.g., sterile pyrogen-free water, before use. The active compounds can also be formulated in rectal compositions such as suppositories or retention enemas, e.g., containing conventional suppository bases such as cocoa butter or other glycerides.

In addition to the formulations described previously, the active compounds can also be formulated as a depot preparation. Such long acting formulations can be administered by implantation (for example subcutaneously or intramuscularly) or by intramuscular injection. Thus, for example, the active compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The active compounds of the invention can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0–4, and the like. Salts tend to be more soluble in aqueous or other protonic solvents that are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections. Alternatively, one can administer the compound in a local rather than systemic manner, for example, via injection of the compound directly into a specific tissue, often in a depot or sustained release formulation.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays, as disclosed herein. For example, a dose can be formulated in animal models to achieve a circulating concentration range that includes the EC50 (effective dose for 50% increase) as determined in cell culture, i.e., the concentration of the test compound which achieves a half-maximal inhibition of tumor cell growth in vitro. Such information can be used to more accurately determine useful doses in humans.

It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician.

For administration to non-human animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).The recombinant expression constructs of the present invention are useful in molecular biology to transform cells that do not ordinarily express a hiwi protein to thereafter express this protein. Such cells are useful as intermediates for making cell membrane, nuclear or cytosolic preparations useful, inter alia, drug screening. The recombinant expression constructs of the present invention thus provide a method for screening potentially useful drugs at advantageously lower cost than conventional animal screening protocols. While not completely eliminating the need for ultimate in vivo activity and toxicology assays, the constructs and cultures of the invention provide an important first screening step for the vast number of potentially useful drugs synthesized, discovered or extracted from natural sources each year.

The invention also provides antibodies that are immunologically reactive to the human hiwi gene product or epitopes thereof provided by the invention. The antibodies provided by the invention may be raised, using methods well known in the art, in animals by inoculation with cells that express a human hiwi gene product or epitopes thereof, cell membranes from such cells, whether crude membrane preparations or membranes purified using methods well known in the art, cytosolic preparations, or purified preparations of proteins, including fusion proteins, particularly fusion proteins comprising epitopes of the human hiwi gene product of the invention fused to heterologous proteins and expressed using genetic engineering means in bacterial, yeast or eukaryotic cells, said proteins being isolated from such cells to varying degrees of homogeneity using conventional biochemical methods. Synthetic peptides made using established synthetic methods in vitro and optionally conjugated with heterologous sequences of amino acids, are also encompassed in these methods to produce the antibodies of the invention. Animals that are useful for such inoculations include individuals from species comprising cows, sheep, pigs, chickens, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses the human hiwi gene product provided by the invention, or more preferably any cell or cell line that expresses the human hiwi gene product of the invention, or any epitope thereof, as a result of molecular or genetic engineering, or that has been treated to increase the expression of an endogenous or heterologous human hiwi gene product by physical, biochemical or genetic means. Preferred cells are mammalian cells, most preferably cells syngeneic with a rodent, most preferably a mouse host, that have been transformed with a recombinant expression construct of the invention encoding a human hiwi gene product, and that express the gene product therefrom.

The present invention also provides monoclonal antibodies that are immunologically reactive with an epitope derived from a human hiwi gene product of the invention, or fragment thereof. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing a human hiwi gene product of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from which spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a human hiwi gene product of the invention. The present invention also encompasses fragments, including but not limited to F(ab) and F(ab)'$_2$ fragments, of such antibody. Fragments are produced by any number of methods, including but not limited to proteolytic or chemical cleavage, chemical synthesis or preparation of such fragments by means of genetic engineering technology. The present invention also encompasses single-chain antibodies that are immunologically reactive with an epitope of a human hiwi gene product, made by methods known to those of skill in the art.

The present invention also encompasses one or a plurality epitope of a human hiwi gene product of the invention, comprised of sequences and/or a conformation of sequences present in the molecule. This epitope may be naturally occurring, or may be the result of chemical or proteolytic cleavage of a human hiwi gene product and isolation of an epitope-containing peptide or may be obtained by chemical or in vitro synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to a human hiwi gene product-derived epitope. The chimeric antibodies embodied in the present invention include those that are derived from naturally occurring antibodies as well as chimeric antibodies made by means of genetic engineering technology well known to those of skill in the art.

The invention also provides methods for maintaining or increasing the number of primitive CD34$^+$ hematopoietic stem cells in peripheral blood culture or in vitro bone marrow culture. During steady state hematopoiesis, most stem cells are quiescent or cycling extremely slowly (Ando et al., 1993, *Proc. Natl. Acad. Sci. USA* 90:9571–9575; Abkowitz et al., 1995, *Proc. Natl. Acad. Sci. USA* 92:2031–2035; Abkowitz et al., 1996, *Nature Med.* 2:190–197; Uchida et al., 1996, *Blood* 88:1297–1305; Morrison et al., 1997, *Proc. Natl. Acad. Sci. USA* 94:1908–1913;

Cheshier et al., 1999, *Proc. Natl. Acad. Sci. USA* 96:3120–3125). Stem cell quiescence may be a passive process involving the absence of proliferation or an active process that occurs as a consequence of a variety of negative inhibitors of hematopoiesis (Akazawa et al., 1992, *J. Biol. Chem.* 267:21879–21885; Bradford et al., 1997, *Exp Hematol.* 25:445–453; Postigo et al., 1997, *EMBO J.* 5:3935–3943). The observation that hiwi expression is associated with diminished proliferation of an immortalized leukemia cell line suggests that the expression of this gene might play a role in maintenance of stem cell quiescence or down regulation of stem cell or progenitor cell cycling. This is somewhat surprising since it has been reported that piwi causes cellular division within a *Drosphila* based model (Cox et al., 2000, *Development* 127:503–514). In *Drosophila*, piwi is expressed both in the terminal filament cells and the germ line. The piwi gene in the terminal filament functions to affect stem cell self-replication while piwi expression in the germ line does not appear to be required for GSC self-replication (Cox et al., 1998, *Genes Dev.* 12:3715–3727). Many of the regulatory signals that control stem cell development are dependent upon cellular interactions between marrow stroma and hematopoietic stem cells (Dexter et al., 1977, ibid.; Wineman et al., 1996, ibid.). Although hiwi was expressed in marrow CD34$^+$ cells, it was not expressed by marrow stroma or marrow mesenchymal stem cells that are capable of differentiating into not only marrow stroma but also other componemts of the hematopoietic niche such as adipocytes, osteoblasts, tenoblasts and cartilage forming cells (Pittenger et al., 1999, ibid.). The data disclosed herein indicate that the potential role of hiwi in human stem cell development is quite different from that which occurs in the *Drosophila* model, and that the hiwi present in CD34$^+$ cells may play a role as an intrinsic regulator of stem cell self-replication.

Thus, the invention provides a method for increasing the percentage of primitive CD34$^+$ hematopoietic stem cells in an in vitro bone marrow culture or peripheral blood culture. In one embodiments, the inventive method comprises the step of culturing the bone marrow or peripheral blood culture cells in the presence of a hiwi gene inducing compound of the invention. In alternative embodiments, the inventive method comprises the step of introducing into the cell a recombinant expression construct of the invention encoding a hiwi gene, most preferably a human hiwi gene. In preferred embodiments, hiwi gene expression mediated by the recombinant expression construct is inducible gene expression.

The Examples that follow are illustrative of specific embodiments of the invention, and various uses thereof. They set forth for explanatory purposes only, and are not to be taken as limiting the invention.

EXAMPLE 1

Cell Culture Preparations and Assays

Isolation of Human and Baboon CD34$^+$ Cells

CD34$^+$ bone marrow cells contain hematopoietic stem and early progenitor cells, in contrast to CD34$^-$ cells, which are predominantly composed of more differentiated precursor cells. Adult human bone marrow (BM) samples (15 to 30 mL) were aspirated from the posterior iliac crests of normal donors after informed consent was obtained according to established guidelines. Heparinized marrow aspirates were diluted with Ca$^{++}$- and Mg$^{++}$-free Dulbecco's phosphate-buffered saline (DPBS) (BioWhittaker, Walkersville, Md.). Diluted marrow was then underlaid with Ficoll-Paque (Pharmacia AB, Uppsala, Sweden), and centrifuged at 800×g for 30 minutes at 20° C. The mononuclear cell fraction was collected and CD34$^+$ cells were immunomagnetically enriched using the MACS CD34 Isolation Kit (Miltenyi Biotec, Auburn, Calif.) according to the manufacturer's instructions. Briefly, cells were incubated with hapten-labeled anti-CD34 antibody (QBEND-10, Becton Dickinson) in the presence of blocking reagent, human IgG (Bayer Corporation Elkhart, Ind.), and then with anti-hapten coupled to MACS microbeads. Labeled cells were filtered through a 30 µm nylon mesh and separated using a high-gradient magnetic separation column. Magnetically retained cells were eluted and stained with CD34$^+$ specific monoclonal antibodies (MoAb) and analyzed using flow cytometric methods. The flow-through population was identified as CD34$^-$ cells. The purity of the CD34$^+$ population was routinely greater than 90%.

BM aspirates were obtained from the humeric and iliac crests of juvenile baboons (*Papio anubis*) after ketamine (10 mg/kg) and xylazine (1 mg/kg) anesthesia. Heparinized marrow was diluted 1:15 in phosphate-buffered saline (PBS) and the mononuclear cell fraction obtained by centrifugation over 60% Percoll (Pharmacia AB) at 500×g for 30 minutes at 20° C. Antihuman CD34 monoclonal antibody K6.1 (a gift from the Naval Medical Research Institute, Bethesda, Md.), a murine IgG$_{2a}$ that cross-reacts with baboon CD34 antigen, was used to select the CD34$^+$ fraction of marrow cells (Davis et al., 1995, *Blood* 85: 1751–1761) This isolated mononuclear cell fraction was suspended in PBS containing 0.2% bovine serum albumin (BSA; Sigma Chemical Co, St Louis, Mo.) and stained first with biotin-conjugated K6.1 (20 µg/mL), washed, and labeled with Miltenyi streptavidin-conjugated iron microbeads (Miltenyi Biotec) and selected as described above according to manufacturer's instructions.

Flow Cytometric Analysis and Sorting

Isolated human CD34$^+$ cells were further fractionated based upon the expression of CD38 antigen (Terstappen et al., 1991, *Blood* 77: 1218–1227) Nonspecific staining was blocked using 0.1% heat-inactivated human gamma globulin (Bayer). Cells were stained with anti-CD34 MoAb conjugated to fluorescein isothiocyanate (FITC) (Becton Dickinson) and anti CD38 labeled with phycoerythrin (PE) (Becton Dickinson). Control cells were incubated with fluorochrome-conjugated isotype-matched IgG1-FITC (Becton Dickinson) and IgG1-PE (Becton Dickinson). Immediately prior to sorting, propidium iodide (PI) at a concentration of 1 µg/mL was added to identify and exclude nonviable cells. Cells were sorted and analyzed on a FACS-Vantage cell sorter (Becton Dickinson). FITC, PE and PI were excited at a wavelength of 488 nm using an argon ion laser. The CD34$^+$ cells were sorted into CD38$^-$, CD38$^{lo}$, and CD38$^{hi}$ subpopulations. Positive fluorescence for each of the markers was established as fluorescence greater than 99% of isotype-matched irrelevant murine IgG$_1$ controls. Cell aggregates or debris were excluded by forward and 90° light scatter. All staining for analysis and sorting was done in the presence of 0.2% BSA in PBS on ice.

Stroma-Free Expansion Cultures

To promote differentiation of human CD34$^+$ cells, a stroma-free suspension culture was established as described by Bazil et al. (1995, *Blood* 86: 502–511) Tissue culture dishes (35 mm; Corning., Corning, N.Y.) were seeded with 1×10$^6$ CD34$_+$ cells/well in 3 mL of Iscove modified Dulbecco medium (IMDM) (BioWhittaker) containing 10% fetal bovine serum (FBS; Hyclone, Logan, Utah). Cultures were placed at 37° C. in 100% humidified atmosphere of 5% $CO_2$ in air. Cultures received a combination of recombinant cytokines at initiation of the cultures and at 72- to 96-hour intervals; these cytokines included stem cell factor (SCF), interleukin (IL)-3, and granulocyte-colony stimulating factor (G-CSF) all at a concentration of 100 ng/mL (R&D Systems, Minneapolis, Minn.). Cultures were maintained at a cell concentration of $5 \times 10^5$ to $2 \times 10^6$ viable cells/mL.

Leukemia Cell Lines

The following leukemia cell lines were used: TF-1 lymphoblast cell line; Jurkat, a T lymphocyte cell line; CEM, an acute T lymphoblast cell line; BV-173, a B cell precursor cell line; K-562, a chronic myeloid cell line; KG1 and KG1a, acute myeloid cell lines (all obtained through the American Type Culture Collection, Manassas, Va.) and SUPB13, an acute B lymphoblastic cell line (a gift from Steve Smith at the University of Chicago, Chicago, Ill.). The lines were maintained in RPMI 1640 (BioWhittaker) supplemented with 10% heat-inactivated FBS (except for KG1 and KG1a which required the presence of 20% FBS), 2 mM L-glutamine, 100 U/mL penicillin, 1 mg/mL streptomycin (BioWhittaker). In addition, granulocyte/macrophage CSF (GM-CSF; 5 ng/mL) (Pepro Tech, Rocky Hill, N.J.) was added to TF-1 culture. Cell density was maintained at $1 \times 10^5$ to $1 \times 10^6$ viable cells/mL.

Mesenchymal Stem Cells

Mesenchymal stem cells were isolated and expanded from normal human marrow aspirates as described by Pittenger et al. (1999, *Science* 284:143–147). These purified cells were provided commercially by Osiris Therapeutics (Baltimore, Md.).

Stromal Cells

Bone marrow stroma was grown by seeding $1 \times 10^6$ low density bone marrow cells/162 $cm^2$ (Corning) flask in low-glucose Dulbecco modified Eagle medium (DMEM; Mediatech, Herndon, Va.) supplemented with 10% heat-inactivated FBS and 2 mM L-glutamine, 100 U/mL penicillin, 1 mg/mL streptomycin (Dexter et al., 1977, *J Cell Physiol.* 91:335–344; Wmeman et al., 1996, *Blood* 87:4082–4090). Adherent cells were split at confluency and the nonadherent cells were discarded. Adherent cells were passaged 4 times and were then termed marrow stroma (Dexter et al., 1977, ibid.; Wineman et al., 1996, ibid.).

EXAMPLE 2

Cloning of Human Homolog of *Drosophila* piwi Gene (hiwi)

A complementary DNA (cDNA) clone of the human homolog (hiwi) of the *Drosophila melanogaster* piwi gene was prepared as follows.

Hiwi gene expression was detected in $CD34^+$ cells using a semi-quantitative polymerase chain reaction (PCR) assay of reverse-transcribed cellular RNA isolated from immuno-magnetically separated $CD34^+$ and $CD34^-$ cells from non-human primates (*Papio anubis*), and from humans. Total RNA was isolated from FACS-separated hematopoietic, stromal, and mesenchymal cells cultured as described in Example 1 using Trizol reagent (Life Technologies, Gaithersburg, Md.) according to manufacturer's instructions. Cells were pelleted and then resuspended in 1 mL of Trizol per $5 \times 10^6$ cells by repeated pipetting. The cell lysate was then incubated for 5 minutes at room temperature and extracted with 0.2 volumes of chloroform by vortexing for 1 minute. The sample was thereafter centrifuged for 30 minutes at 13,000 rpm (12,000 g), 4° C. in a microcentrifuge. The RNA was precipitated using 2 volumes isopropanol, mixed and allowed to sit at room temperature for 10 minutes. RNA was centrifuged for 45 minutes at 13,000 rpm (12,000×g). The pelleted RNA was washed with 75% ethanol, briefly dried, and resuspended in RNase-free water or diethyl pyrocarbonate-treated (DEPC; Sigma) water (0.1%). The amount of RNA in the preparation was then quantitated using a DU 650 spectrophotometer (Beckman Instruments, Palo Alto, Calif.). The RNA was treated with DNase I enzyme (Life Technologies) according to the manufacturer's instructions.

Polymerase chain reaction (RT-PCR) amplification was performed on RNA samples using an RNA PCR Core Kit (PerkinElmer, Foster City, Calif.), according to the manufacturer's instruction, except that High Fidelity Platinum Taq DNA Polymerase (Life Technologies) was substituted for AmpliTaq. Alternatively, a Stratagene ProSTAR First-Strand RT-PCR Kit (Stratagene, La Jolla, Calif.) was used for amplification. One microgram of total RNA was used for cDNA synthesis using random hexamers to prime first strand synthesis. The synthesized $CD34^+$ cDNA was divided and used for PCR amplification. As a control, duplicate cDNA synthesis reactions were performed for each experiment without the addition of reverse transcriptase. Control PCR amplification reactions were performed using primers for glyceraldehyde phosphate dehydrogenase cDNA (GAPD; forward primer, 5'-GGCTGAGAACGGGAA-GCTTGTCAT-3' (SEQ ID NO.: 3); reverse primer, 5'-CAGCCTTCTCCATGGTGGTGAAGA-3' (SEQ ID NO.: 4)) for 1 cycle at 94° C./2 min; 5 cycles at 94° C./10 s, 70° C./2 min; 5 cycles at 94° C./10 s, 68° C./2 min; 25 cycles at 94° C./10 s, 66° C./2 min, and 1 cycles at 72° C./10 min and produced a 142-bp product. $\beta_2$ microglobulin primers were also used as an internal control ($\beta_2$ microglobulin: forward primer, 5'-CTCGCGCTACTCTCTCTTTC-3 (SEQ ID NO. 5); reverse primer, 5'-CATGTCTCGATCCCACTTAAC-3' (SEQ ID NO. 6)) producing a 329-bp product. PCR amplification primers were designed based on the partial published hiwi DNA sequence found in the Genbank database (accession number AF104260). Detection of hiwi in $CD34^+$ DNase treated RNA was performed using the primer pair hiwiF269 5'-GAAGCAGCCTGTCTTGGTCAGC-3' (SEQ ID NO. 7) and hiwiR269 5'-GAATCAAAGCTCAAACCCCA-GTCTC-3' (SEQ ID NO. 8) producing a 269 bp product.

The semiquantitative RT-PCR assay produced a hiwi-specific 269 bp DNA fragment 269 bp from $CD34^+$ cells; an identically-sized fragment was also found after RT-PCR amplification of human testis cDNA. This fragment was specific for cDNA prepared from $CD34^+$ cells and was not observed after amplification of $CD34^-$ cell cDNA from either humans or baboons. Direct DNA sequencing of the PCR product was performed using an ABI Prism Dye Terminator Cycle Sequencing Reaction Kit (PerkinElmer) according to the manufacturer's instructions. Additional primers (Integrated DNA Technologies, Coralville, Iowa) were synthesized based upon analyzed sequence in order to obtain the complete cDNA sequence. This analysis confirmed that the PCR product fragment was a fragment of the hiwi cDNA (FIG. 1).

To examine whether hiwi gene expression was restricted to the most primitive subpopulation of human $CD34^+$ cells, $CD34^+$ cells were sorted according to CD38 expression into 3 subpopulations: $CD34^+CD38^-$, $CD34^+CD38^{lo}$, $CD34^+CD38^{hi}$ (FIG. 2A). Semiquantitative RT-PCR on DNase treated RNA isolated from each population showed that each of the 3 subpopulations expressed hiwi. These data indicate the hiwi expression is not limited to the most primitive progenitor cell population (FIG. 2B).

The full-length human hiwi gene was cloned as follows. A primer pair that spanned from amino acid 364 to 524 of the published partial coding sequence was designed and produced a 480-bp fragment that corresponded to the C-terminal end of the protein. After positively identifying the PCR product to be that of hiwi through dye terminator cycle sequencing (Sambrook et al., 2001, ibid.), primers were designed to amplify the potential full length gene from human testis cDNA by using a 5' RACE cloning methodology that allows the PCR amplification of a given gene of interest by utilizing a small region of a known sequence. Two primer pairs were designed to be employed in 5' Rapid Amplification of cDNA Ends (5' RACE) PCR strategy cloning (Chenchik et al., 1996, *Biotechniques*. 21:526–534):

AKSrev1, reverse primer #1: 5'-CGCTGTATGT-GGTCTGGCTTCAGGC-3' (SEQ ID NO. 9) and
AKSrev2, reverse primer #2; 5'-GGGAGAAACACTA-CCACTTCTCACAGCCTG-3' (SEQ ID NO. 10).

AKSrev2 is located 32 nucleotides upstream from AKSrev1 and serves as a nested internal control for secondary PCR amplification. AKSrev1 and AKSrev2 were also based upon the published partial hiwi coding sequence and acted as a nested primer pair for primary and secondary PCR amplification reactions and correspond to base pairs 1391 to 1415 and 1330 to 1359, respectively. Marathon Ready Human Testis cDNA Kit (Clontech Laboratories, Inc., Palo Alto, Calif.) was used for primary amplification, according to manufacturer's instructions. First round PCR amplification consisted of AKSrev1 and AP-1 (5'-CCATCCTAATACGACTCACTATAGGGC-3' (SEQ ID NO. 11), supplied within the cDNA Kit) under the following conditions: 1 cycle at 94° C./2 min; 5 cycles at 94° C./10 s, 71° C./2 min; 5 cycles at 94° C./10 s, 69° C./2 min; 25 cycles at 94° C./10s, 67° C./2 min, and 1 cycle at 72° C./10 min. A single PCR product was separated on a 1% SeaPlaque Agarose (FMC, Rockland, Me.) 1× TAE gel stained with ethidium bromide and purified from the agarose using a Wizard PCR Prep Kit (Promega Corporation, Madison, Wis.). The isolated PCR fragment was then used in a second round of PCR amplification that utilized the same PCR amplification conditions listed above except that AKSrev2 was substituted for AKSrev1 and AP-2 (5'-ACTCACTATAGGGCTCGAGCGGC-3' (SEQ ID NO. 12) replaced AP-1. All PCR reactions were performed in a PerkinElmer Thermal Cycler 9700 (Perkin Elmer) or Stratagene Robocycler Gradient 96 Thermal Cycler.

After employing the 5' RACE methodology on the human testis cDNA sequence and two rounds of PCR amplification (the second round consisting of a nested PCR amplification) a putative 2.3 kb full length coding sequence was cloned. After several rounds of sequencing through primer walking, an open reading frame was determined, and is shown in FIG. 1 (SEQ ID NO. 1). When compared to the Genbank database of non-redundant clones, the human HIWI protein (SEQ ID NO>2) showed a 52% homology to the *Drosophila* PIWI protein (SEQ ID NO. 13) at the amino acid level (FIG. 1).

Primer pairs were then designed to amplify the full length coding sequence from $CD34^+$ hematopoietic cell cDNA through PCR amplification. Based upon a sequence obtained from the human testis clone, primers were designed to amplify a putative full-length cDNA clone, FLhiwifor1 (forward primer, 5'-ATGATCTTTGGTG-TGAACACAAGGCAGAA-3' (SEQ ID NO. 14) and
FLhiwirev1 (reverse primer, 5'-GAGGTAGTAAAGG-CGGTTTGACAGTGACAGA-3' (SEQ ID NO. 15).

PCR amplification conditions were as follows: 1 cycle at 94° C./2 min; 5 cycles at 94° C./10 s, 72° C./2 min; 5 cycles at 94° C./10 s, 70° C./2 min; 25 cycles at 94° C./10s, 68° C./2 min, and 1 cycle at 72° C./10 min. A 2.3 kb band was detected in the $CD34^+$ cDNA sample but not in the no-template control. No bands were detectable in the absence of reverse transcriptase (-RT) during the cDNA synthesis step. Control PCR amplification with primers specific for glyceraldehyde phosphate dehydrogenase (GAPD) confirmed that the quantity and integrity of the RNA could be PCR amplified. The PCR product was sequenced and the identity was confirmed to be that of the hiwi gene by comparing it to the Genbank database.

After obtaining the full-length hiwi cDNA, the fragment was then subcloned into the XhoI/NotI sites of the pCIneo Mammalian Expression Vector (Promega) and used for expression studies as described below.

EXAMPLE 3

Recombinant Expression of Cloned Human hiwi Gene

Figure 3:
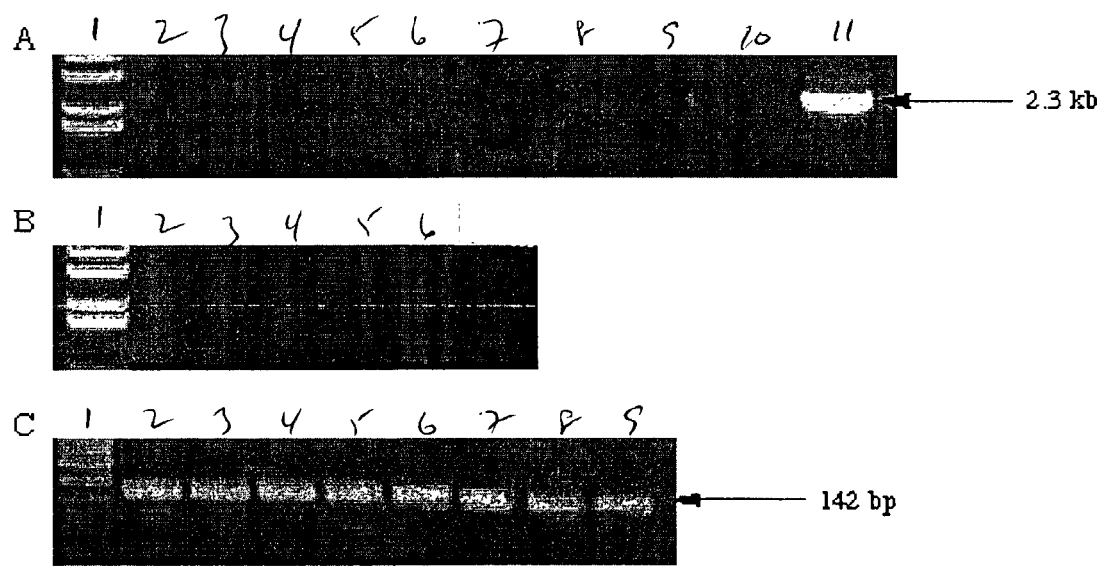

A human leukemia cell line, KG1 cells were chosen as recipients for recombinant human hiwi production due to their lack of expression of the hiwi mRNA as demonstrated by RT-PCR (FIG. 3). A recombinant expression construct encoding human hiwi was introduced into these cells by electroporation. Electroporation of plasmid DNA into KG1 cells was accomplished using a Bio-Rad Gene Pulser II System (Bio-Rad Laboratories, Hercules, Calif.) under conditions of 300 V and 950 $\mu$F using a 0.4 cm gapped cuvette (Bio-rad Laboratories). Fifty micrograms of pCIneo or pCIneo-hiwi was electroporated per $1 \times 10^5$ KG1 cells, accompanied with 2 $\mu$g of linearized vector for each respective condition as well as a mock control that consisted of KG1 cells alone. All cells were washed with and then resuspended in DPBS prior to electroporation. Cells were then centrifuged and washed twice with DPBS and resuspended in IMDM supplemented with 20% heat inactivated FBS, 100 U/mL penicillin, 1 mg/mL streptomycin, and 2 mM L-glutamine and incubated overnight at 37° C. in a 100% humidified incubator containing 5% $CO_2$ in air. After overnight incubation, cells were counted and stained for viability using a 0.4% trypan blue solution (Sigma) on the following day. Cells were then plated at a density of $2 \times 10^4$ viable cells per well in a flat bottom 96 well plate (Corning) in IMDM supplemented with 5% heat inactivated FBS, 100 U/mL penicillin, 1 mg/mL streptomycin, and 2 mM L-glutamine. Similar populations of cells (pCIneo vector alone, the pCIneo-hiwi, or cells alone) were incubated in IMDM supplemented with 20% FBS, 100 U/mL penicillin, 1 mg/mL streptomycin, and 2 mM L-glutamine containing 1 mg/mL Geneticin Selective Antibiotic (G418 sulfate; Life Technologies) for 3 weeks. Several sets of transfected cells were plated under similar conditions for detection of the hiwi gene by PCR and for antibiotic selection. G418 resistant colonies were assayed by RT-PCR for expression of human hiwi mRNA.

The proliferative capacity of KG1 cells expressing the recombinant human hiwi gene was determined using an MTT exclusion assay. In this assay, cell proliferation and survival was measured by cellular uptake of MTT{(3,-[4,5-dimethylthiazol-2-yl]-2,5-diphenyltetrazolium bromide; Sigma-Aldrich),. which measures living cells (Bazil et al., 1995, ibid.). Fifty microliters of a 1 mg/mL solution of filter sterilized MTT in DPBS was added to each culture volume of 200 μL containing $2\times10^4$ viable cells per well and then incubated for 4 hours at 37° C. in a 100% humidified incubator, 5% $CO_2$ in air. Approximately half of the volume was then carefully removed (without disrupting the solubilized complex) and replaced with developing reagent that consisted of 40 mM hydrochloric acid in isopropanol. After thoroughly homogenizing the solubilized complex with the developing reagent, the plate was then read on an ELX-800 ELISA plate reader (Bio-Tek Instruments, Winooski, Vt.) at wavelength of 570 nm with a reference wavelength of 630 nm as previously described (Sharma et al., 2001, *Blood* 97: 426–434). This procedure was performed on days 1 to 6 and then on day 9.

Figure 5:
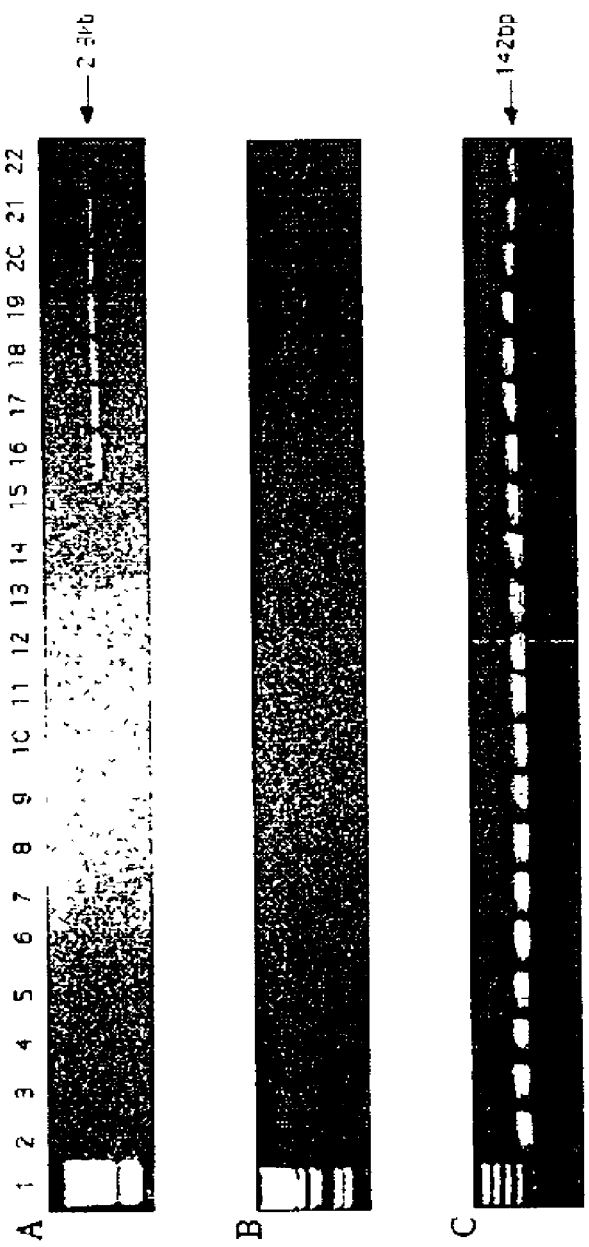

The results of these assays are shown in FIG. 4. As shown in the Figure, the proliferative capacity of mock transfected and pCIneo vector treated cells was similar. KG1 cells transfected with either the empty vector control or the mock transfection control were capable of proliferating normally without the presence of the hiwi gene or interference from the empty vector control. However, KG1 cells transfected with the pCIneo-hiwi construct showed greatly diminished proliferation. To determine whether the diminished proliferation was accompanied by hiwi gene expression in the transfected cells, RT-PCR analysis was performed as described above. These assays, the results of which are shown in FIG. 5, demonstrated the presence of the hiwi transcript from day 1 (24 hours post transfection) until cultures were terminated (day 9). The declining levels of the expressed gene was likely due to the fact that the cells were not subjected to G418 antibiotic selection during the assay.

To further assess the function and integrity of each construct, populations of cells that had been simultaneously transfected were placed in the presence of 1 mg/mL of active G418 for 3 weeks. After this period, the pCIneo-hiwi construct and the pCIneo empty vector contained similar numbers of viable cells. The pCIneo-hiwi construct further continued to express the hiwi gene (as determined by PCR). The mock transfected cells were, however, characterized by a high degree of cell death at day 6 (>96%, data not shown). These results demonstrate that both the cytomegalovirus (CMV) promoter and the SV40 promoter (which was driving neomycin phosphotransferase gene) were actively driving transcription of their respective genes and that hiwi gene expression was present, but to an unknown level.

The cause of the observed reduced proliferative capacity of KG1 cells that overexpress the hiwi gene product was also investigated by examining apoptosis (programmed cell death) of these cells. Apoptosis was evaluated using Annexin V as an indicator of programmed cell death and PI as a measure of cell viability. KG1 cells were transfected under the three separate conditions as previously described. Condition 1 consisted of a mock transfection, condition 2 consisted of an empty vector control transfection, and condition 3 consisted of the vector containing hiwi. An additional sample of KG1 cells was also serum starved for 24 hours in IMDM, 2 mM L-glutamine, 100 U/mL penicillin, and 1 mg/mL streptomycin (BioWhittake). Incubation conditions are similar to those described above. Transfected cells were maintained in culture for up to 32 hours and then assayed for programmed cell death by the Annexin V Assay System (Pharmingen, San Diego, Calif.) according to the manufacturer's instructions. Briefly, cells were washed with DPBS, collected and then resuspended in binding buffer containing Annexin V-FITC and PI at room temperature. Acquisition and analysis of data was performed by FACS on a FACSCalibur (Becton Dickinson) using the CellQuest Analysis Software (Becton Dickinson).

FIGS. 6D–F shows the results of such an analysis after an 8 hour incubation, and demonstrates an approximate 4.4 fold increase (9.6%) in the percentage of cells undergoing apoptosis, (positive for Annexin V but negative for PI) when compared to the mock (1.8%) and the empty vector control (2.4%). The degree of apoptosis after 12 hours of incubation is also greater in the hiwi overexpressing cells as compared to the control cells. Flow cytometric analysis at 32 hours of culture (FIGS. 6J–L) exhibited an increase in the number of cells that were PI and Annnexin positive suggesting that the cells had proceeded to a necrotic state. These data indicate that the majority of the cell population containing the hiwi gene underwent apoptosis and eventually entered a terminal state of cell death. The rapid progression of apoptosis can be seen at the 8-hour timepoint where a majority of the cells in the hiwi containing population have undergone apoptosis and have started to proceed into the necrotic state. These studies suggest that hiwi overexpression causes programmed cell death. Lack of apoptosis in the cells transfected with the hiwi gene which were maintained in selective media maybe due to the SV40 promoter, (which drives the transcription of the neomycin phosphotransferase gene), out competing the CMV promoter (that directs the transcription of the hiwi gene) because of the selective pressure placed upon the SV40 promoter by the G418 selection. This may account for diminished expression of the hiwi gene product while the transcription of the neomycin phosphotransferase gene continues. Emerman et al (1984, *Cell* 39:449–467) have reported a state of gene suppression in cells genetically modified with a retrovirus in which one gene is shutdown while the second gene undergoes normal transcription due to promoter competition. Because the KG1 cells were electroporated and put into media that was lacking G418 for the apoptosis experiments, there would be no need for the activation of the SV40 promoter allowing the CMV to transcribe the hiwi gene unperturbed, thus allowing for the rapid induction of apoptosis resulting in eventual cell death. This study indicates that hiwi inhibits KG1 cell proliferation and therefore suggests that this gene may play a role in the negative regulation of hematopoietic cells.

EXAMPLE 4

Cell and Tissue Expression of Human hiwi Gene

Human hiwi gene expression was assayed in a variety of human cells and tissues.

To determine the expression pattern of hiwi in various adult and fetal tissues other than $CD34^+$ marrow cells, PCR amplification was performed using hiwi specific primers on cDNA samples (Clontech Laboratories). Fetal cDNA samples ranged from 18 to 36 weeks of gestation. The expression level was determined through semiquantitative PCR amplification. PCR amplification was performed on 3 different Multiple Tissue cDNA Panels: human I, human II, and human fetal (Clontech Laboratories). The following PCR conditions were used for amplification with primer pair:

GSP2F4 (forward primer, 5'-CCTTGCCAGTACG-CCCACAAGCTG-3' (SEQ ID NO. 16) and

GSP1R1966 (reverse primer, 5'-CCCCACCTATGGTTGT-AGTGAGCATCC-3' (SEQ ID NO. 17)
PCR amplification conditions used were: 1 cycle at 94° C./2 min; 35 cycles at 94° C./10 s, 70° C./15 s, 72° C./45 s and 1 cycle at 72° C./10 min which produced a 557 bp product. Positive samples were separated on a 1% SeaPlaque Agarose (FMC) 1× TAE gel stained with ethidium bromide and purified from agarose using the Wizard PCR Prep Kit according to the manufacturer's instructions. Asymmetric restriction endonuclease digestion was performed to determine the identity of the PCR products.

The results of this analysis revealed a wide distribution of hiwi through most fetal and adult tissues (FIGS. 7A and 7B). The highest level of expression in fetal tissues (FIG. 7A) was found in the kidney. Analysis of adult samples (FIG. 7B) showed that hiwi was also expressed in a wide range of tissues such as the prostate, ovary, small intestine, heart, brain, liver, skeletal muscle, kidney and pancreas. The highest level of expression was seen in the testis followed by the kidney. Expression of hiwi was not detected in mesenchymal stem cells or marrow stroma.

Human leukemia cell lines were also assayed for human hiwi expression. Because leukemia is frequently accompanied by expansion of the hematopoietic compartment, it was anticipated that leukemia cells would express hiwi, a gene that is associated with self-replication. A variety of immortalized human leukemia cell lines belonging to various lineages were examined; these results are shown in FIGS. 3A through 3C. Analysis of eight immortalized leukemia cell lines showed that the hiwi mRNA transcript was not detectable by RT-PCR. These results suggested that hiwi gene expression may not be a component of the genetic program that accompanies leukemogenesis. As disclosed above, hiwi gene expression appears to be limited within the hematopoietic compartment to normal $CD34^+$ cells. This data indicates that the lack of hiwi expression may be a consequence of and a marker for the leukemic transformation event.

The effect on $CD34^+$ expression of cell differentiation was also examined. $CD34^+$ cell differentiation was promoted in a suspension culture system to which SCF, IL-3, and G-CSF were added each at 100 ng/mL every 3–4 days. Bazil and colleagues (Bazil et al., 1995, Blood 86: 502–511) have previously shown these conditions allow for rapid proliferation and differentiation causing the cells to leave the $CD34^+$ compartment. Aliquots of cells were harvested on days 0, 1, 3, 5, 7, 10, and 14 and analyzed flow cytometrically for $CD34^+$ expression and by semi-quantitative RT-PCR for the hiwi messenger RNA (mRNA) (results shown in FIG. 8A). On day 0, the starting cell population was composed of 99% $CD34^+$ cells. Day 5 $CD34^+$ content diminished to 20% of the expanded cell population; by day 7, fewer than 0.1% of the cells were $CD34^+$ while by day 10 there were no detectable $CD34^+$ cells present. By day 3, hiwi expression was markedly reduced and no longer detectable by semiquantitative RT-PCR by day 5. Concurrently $\beta_2$ microglobulin gene expression was used as an internal control. $\beta_2$ microglobulin levels remained constant throughout the 14 days of culture (FIG. 8B).

These results indicate that hiwi expression is unique to the more primitive cellular compartment and that its expression might serve as a genetic marker of progenitor and stem cells.

EXAMPLE 5

Chromosome Mapping of the Human hiwi Gene

The chromosome location of hiwi was determined by Sequence Tagged Site (STS) computer based mapping (Taymans et al., 1999, Genomics 56:344–349; Stringham et al., 1999, Am J Hum Genet. 65:545–553). Four different STS clones (Genbank accession numbers AA639672, AA904973, AA969660, and A125224) were found to have significant homology to the hiwi gene. These 4 clones, along with the partial published hiwi sequence were then mapped to the reference interval of D12S340–D12S97 (147.5–160.9 cM) by radiation hybridization (Unigene cross-reference Hs. 128673). The physical position of hiwi was located at 489.71 cR3000 (P1.43, stSG53541) on the q arm of chromosome 12, specifically between 12q24.2 through 12q24.32 as represented by the cytogenetic ideogram.

To directly determine the chromosomal location of the human hiwi genetic locus, a hiwi genomic clone was hybridized on metaphase chromosomes derived from a human peripheral blood cell culture. Identification of the human chromosomes was based on their DAPI-banding pattern that resembles G-bands achieved by conventional trypsin-Giemsa treatment. Thirty two metaphase spreads were analyzed; a representative spread is shown in FIG. 9. These results showed specific localization to chromosome 12 as follows: specific hybridization signals were seen 9 times (28.1%) in two chromatids, 10 times (31.3%) in three chromatids and 11 times (34.4%) in four chromatids, no hybridization signals were seen in two metaphases (6.2%). A very small number of non-specific hybridization sites were seen (9). Traditional FISH analysis confirmed the computer based chromosomal localization of hiwi.

The physical locale of hiwi does not currently show an association with any hematological disorders (as demonstrated by STS/EST homology comparisons).

EXAMPLE 6

Transduction of Human Hematopoietic Stem Cells

Human hematopoietic stem cells were transduced using a recombinant retrovirus to induce constitutive human hiwi gene expression introduced in the cells.

Retrovirus encoding human hiwi were produced by cloning the human hiwi gene described in Example 2 into a bicistronic mouse stem cell virus (MSCV) based vector genome that encodes the yellow fluorescent protein (YFP) under the control of the internal ribosome entry site (IRES). Producer cells were derived from the PG13 packaging cell line obtained from the American Type Culture Collection (ATCC; Manassas, Va.). Producer cells were generated by transfecting the cells with hiwi and YFP-encoding cloned retrovirus. Retroviral vector particles were pseutotyped with the gibbon ape leukemia virus (GALV) envelope protein. The vector producing cell line was initially grown in Dulbecco's modified Eagle's medium (DMEM; BioWhittaker) containing 10% FBS and then slowly adapted to IMDM containing 10% FBS. Cells were cultured at 37° C. in 5% $CO_2$.

Human bone marrow cell aspirates were prepared as described in Example 1. $CD34^+$ purified cell populations were cultured in IMDM supplemented with 10% FBS, 2 mM L-glutamine, 100 U/mL penicillin, and 1 mg/mL streptomycin. Cells were cultured for 24 hours at 37° C. in 5% $CO_2$ before transduction in the presence of the following cytokines: stem cell factor (SCF; 300 ng/mL), Flt-3 ligand (300 ng/mL), interleukin-3 (IL-3; 10 ng/mL) and interleukin-6 (IL-6; 10 ng/mL); all cytokines were obtained from R&D Systems, Minneapolis, Minn. Immunoselected cells were then plated at a density of $2-4 \times 10^4$ cells per well of a 48 well plate coated with 20 ug/cm² recombinant human FN fragment CH-296 (Retronectin; Panvera, Madison, Wis.). Fresh retroviral supernatant and cytokines were added to the cells once a day for 4 consecutive days. On the last day of culture, cells were harvested and then analyzed flow cytometrically for CD34 and YFP expression.

Transduced human CD34$^+$ cells were analyzed for CD34 and YFP expression. Cells were stained with anti-CD34 MoAb conjugated to allophycocyanin (APC; Becton Dickinson). Control cells were incubated with fluorochrome conjugated isotype matched IgG1-APC (Becton Dickinson). Prior to sorting, 1 ug/mL propidium iodide (PI) was added to each sample to identify and exclude nonviable cells. Cells were sorted on a FACSVantage cell sorter (Becton Dickinson); APC was excited at 633 nm and YFP expression was determined at an excited wavelength of 488 nm using an argon ion laser. Positive fluorescence for each of the markers was established as fluorescence greater than 99% of isotype-matched irrelevant murine IgG$_1$ controls. Cell aggregates or debris were excluded by forward and 90° light scatter. All staining for analysis and sorting was done in the presence of 0.2% BSA in PBS on ice.

The results of flow cytometric analysis of a CD34$^+$ cell population that was transduced with the hiwi-containing retrovirus revealed an increase in the number of cells that retained the primitive CD34 antigen as well as the YFP expression marker. This approximate 7% retention of primitive stem cells was derived from comparing the hiwi expressing population to an identically transduced population containing the MSCV retroviral empty vector. FIG. 10 shows flow cytometric analysis demonstrating virtually no CD34$^+$ YFP$^+$ cells in the empty vector control (minus the background from the empty vector isotype control) while the hiwi-containing vector shows a seven fold increase (minus the background from the hiwi isotype control). This analysis was based upon approximately 7,000 gated events.

It should be understood that the foregoing disclosure emphasizes certain specific embodiments of the invention and that all modifications or alternatives equivalent thereto are within the spirit and scope of the invention as set forth in the appended claims.

What we claim is:

1. A isolated nucleic acid comprising a nucleotide sequence encoding a human hiwi gene having a necleotide sequence that encodes the amino acid sequence identified by SEQ ID NO.2.

2. An isolated nucleic acid probe comprising the nucleotide sequence identified by SEQ ID No. 1.

3. A recombinant expression construct comprising a nucleic acid comprising a nucleotide sequence encoding a human hiwi gene according to claim 1, wherein the construct is capable of expressing the human hiwi gene product in a transformed culture of eukaryotic or prokaryotic cells.

4. A cell culture transformed with the recombinant expression construct of claim 3 wherein the transformed cell culture expresses the human hiwi gene.

5. A method of screening a compound for modulating human hiwi gene activity in cells expressing the human hiwi gene product, the method comprising the steps of:
   (a) producing a transformed cell culture by transforming host cells with a recombinant expression construct gene according to claim 3, wherein the cells of the transformed cell culture express the human hiwi gene product; and
   (b) assaying the transformed cell culture with the compound to determine whether the compound modulates activity of the human hiwi gene product.

6. A method of claim 5 comprising the additional step of:
   (c) comparing the compound's modulation of human hiwi gene activity with modulation mediated by additional compounds that are known to modulate human hiwi gene activity.

* * * * *